United States Patent
Goswami et al.

(10) Patent No.: US 7,029,835 B2
(45) Date of Patent: Apr. 18, 2006

(54) PHOTOTHERMOGRAPHIC ELEMENT COMPRISING IMPROVED BASE PRECURSORS AND METHODS FOR THEIR USE

(75) Inventors: Ramanuj Goswami, Webster, NY (US); David H. Levy, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 42 days.

(21) Appl. No.: 10/765,340

(22) Filed: Jan. 27, 2004

(65) Prior Publication Data

US 2004/0185352 A1 Sep. 23, 2004

Related U.S. Application Data

(62) Division of application No. 10/300,552, filed on Nov. 20, 2002, now Pat. No. 6,699,651.

(51) Int. Cl.
*G03C 1/815* (2006.01)
*G03C 1/825* (2006.01)

(52) U.S. Cl. ............... 430/350; 513/516; 513/529; 513/619; 513/955; 513/959

(58) Field of Classification Search ............... 430/350, 430/513, 516, 529, 619, 955, 959
See application file for complete search history.

(56) References Cited

U.S. PATENT DOCUMENTS

| 4,207,392 A | | 6/1980 | Shiao et al. |
| 4,981,965 A | * | 1/1991 | Yabuki et al. ............ 544/196 |
| 5,314,795 A | * | 5/1994 | Helland et al. ........... 430/517 |
| 6,368,782 B1 | | 4/2002 | Fukui et al. |

FOREIGN PATENT DOCUMENTS

| DE | 35 30 063 A1 | 3/1986 |
| DE | 35 30 214 A1 | 3/1986 |
| EP | 0 308 750 | 3/1989 |
| GB | 2 058 383 A | 4/1981 |

* cited by examiner

*Primary Examiner*—Thorl Chea
(74) *Attorney, Agent, or Firm*—Chris P. Konkol

(57) ABSTRACT

Photothermographic elements employing improved base precursors that undergo thermal decomposition are disclosed. Thermal-dye-bleach agents, and in particular, a novel class of salts of arylsulfonylacetic acids as bleaching agents for photothermographic use are disclosed. Photothermographic elements employing these thermal-dye-bleach agents are suitable for use as acutance and antihalation systems, bleachable filter dye materials, and in promoting unblocking of various components such as blocked developers, especially in photothermographic elements.

20 Claims, No Drawings

PHOTOTHERMOGRAPHIC ELEMENT COMPRISING IMPROVED BASE PRECURSORS AND METHODS FOR THEIR USE

CROSS-REFERENCE TO RELATED APPLICATIONS

This is a divisional of application Ser. No. 10/300,552, filed Nov. 20, 2002 now U.S. Pat. No. 6,699,651.

FIELD OF THE INVENTION

This invention relates to improved thermal base precursors. Such compounds can be used, for example, in thermally bleachable filter dye compositions or in other components in photothermographic elements.

BACKGROUND OF THE INVENTION

A thermal base precursor is a neutral or weakly basic compound which can generate a strong base during thermal processing. Various base precursors are known as, for example, described in U.S. Pat. Nos. 3,220,846; 4,060,420 and 4,731,321. Japanese Patent Application No. 1-150575 describes thermally-releasable bis-amines in the form of their bis(aryl sulfonylacetic acid)salts. Other amine-generating compounds include 2-carboxycarboxamide derivatives disclosed in U.S. Pat. No. 4,088,469, hydroxime carbamates disclosed in U.S. Pat. No. 4,511,650 and aldoxime carbamates disclosed in U.S. Pat. No. 4,499,180. Examples of some thermal base precursors are shown in Table III of U.S. Pat. No. 5,258,274 to Helland et al., including cations and anions, which patent is incorporated by reference.

Further examples of base precursors include salts of carboxylic acids and organic bases as described in U.S. Pat. No. 3,493,374 (triazine compounds and carboxylic acids), British Patent 998,949 (trichloroacetic acid salts), U.S. Pat. No. 4,060,420 (sulfonylacetic acid salts), JP-A-59-168441 (The term "JP-A" as used herein means an "unexamined published Japanese patent application") (sulfonylacetic acid salts), JP-A-59-180537 (propionic acid salts), JP-A60-237443 (phenylsulfonylacetic acid salts substituted by a sulfonyl group), and JP-A-61-51139 (sulfonylacetic acid salts).

Base precursors consisting of carboxylic acids and organic di or tetra-acidic bases are disclosed in JP-A-63-316760 and JP-A-1-68746 (corresponding to U.S. Pat. No. 4,981,965). In these base precursors, the activity on heat treatment at 140° C. is compatible with the storability. EP0708086 discloses selected base precursors which simultaneously satisfy both the activity on heat treatment at 120° C. or less and the storability.

Base precursors each has an inherent decomposition point. However, in practical applications rapid decomposition of the base precursors (the release of bases) is expected only at heating temperatures much higher than their decomposition points. For example, although ease of the decomposition also is dependent on methods of heating, in order to obtain rapid decomposition at a heating temperature of 120° C., the base precursors must usually have a decomposition point of about 100° C. or less.

Other bisguanidine base precursors that are known are described in EP0708086, hereby incorporated by reference. These base precursors can be employed when it is desirable to rapidly release a base at a low heating temperatures and have good storability at the same time. Such bisguanidine salts are selected from the group consisting of a 4-(phenylsulfonyl)phenylsulfonylacetic acid salt of N,N'bis(1,3-diethylguanyl)ethylenediamine, a 4(phenylsulfonyl)phenylsulfonylacetic acid salt of N,N'-bis(1,3diisopropylguanyl) ethylenediamine, 4(phenylsulfonyl)phenylsulfonylacetic acid salt of N,N'-bis-(imidazoline-2yl)ethylenediamine, and other specified compounds.

Base precursors that are neutral or weakly basic compounds that can form relatively strong bases, in heat developable recording materials, by heat decomposition of the base precursors, are described in U.S. Pat. No. 4,981,965, hereby incorporated by reference. This patent describes base precursors comprising arylsulfonylacetic acid salts of guanidine bases. Such base precursors have a stable crystal structure, which crystal structure is kept until it melts or is dissolved at an elevated temperature. Therefore, the carboxylic acid is rapidly decarboxylated to release a base at the same time that the crystal structure is broken.

When the carboxylic acid has hydrophobic residues, the carboxyl group of the carboxylic acid and the organic base are blocked by the hydrophobic residues in the base precursor of the present invention. Accordingly, the base precursor is prevented by the hydrophobic residue from being dissolved in a binder (which generally is hydrophilic). The crystal structure of the salt is further stabilized by intermolecular interaction between the hydrophobic residues. Therefore, such preferred base precursors for use in the present compositions exhibit much higher stability during storage when the carboxylic acid has the hydrophobic residues. Examples of the carboxylic acid are given in the cited U.S. Pat. No. 4,981,965, in columns 9–10.

U.S. Pat. No. 4,981,965 describes the use of guanidinium salts of arylsulfonylacetic acids as base precursors. The diacidic to tetraacidic base precursors are composed of two to four guanidinium units. In these systems, thermolysis of the salt results in decarboxylation to form a arylsulfonylmethyl anion. This anion abstracts a proton from the guanidinium salt to release the free base. This base can then provide the alkalinity required for a number of image-forming processes.

U.S. Pat. No. 4,060,420 describes the use of ammonium salts of arylsulfonylacetic acids as activator-stabilizers in photothermographic systems. In these systems the ammonium species is always a protonated basic nitrogen, and thus has at least one labile hydrogen atom. U.S. Pat. No. 4,731,321 discloses ammonium salts of arylsulfonylacetic acid as base precursors in heat-developable lightsensitive materials.

Japanese Patent Application No. 1-150575 discloses thermally releasable bisamines in the form of their bis(arylsulfonylacetic acid) salts. Other amine-releasing compounds include 2-carboxycarboxamide derivatives disclosed in U.S. Pat. No. 4,088,496; hydroxylamine carbamates disclosed in U.S. Pat. No. 4,511,650; and aldoxime carbamates disclosed in U.S. Pat. No. 4,499,180.

It is usually desirable for a base precursor to exhibit good stability during storage but to quickly decompose to form a base when it is heated at the temperature of use. A successful base precursor will not have any adverse effects on the adjacent layers.

PROBLEM TO BE SOLVED BY THE INVENTION

There is a need for improved base precursor compositions that can be used to permanently and quickly bleach preselected colored components of in photothermographic systems. Particularly in the field of color photothermographic film for consumer use, the requirements in terms of bleaching and keeping are high.

A problem with prior-art base precursors when used in a filter layer is that they can cause unacceptable increase of fog densities at the adjacent imaging layers during keeping or during thermal processing. Applicants have found that prior-art base precursors can also cause pinholes during thermal processing due to unfavorable diffusion of gas formed during thermal decomposition, rendering the photothermographic element useless. There is a need for color photothermographic imaging element comprising an improved base precursor in combination with a filter dye (especially yellow or magenta filter dye) which undergoes efficient and irreversible thermal bleaching during thermal processing. The existence of such imaging chemistry would allow for very rapidly processed films that can be processed simply and efficiently in low cost photoprocessing kiosks.

These and other problems may be overcome by the practice of our invention.

SUMMARY OF THE INVENTION

As mentioned above, the present invention is directed to improved thermal base precursors. Such compounds can be used, for example, to thermally bleaching filter dyes or other components in photothermographic elements.

This invention also relates to thermal-dye-bleach agents, and in particular, it relates to salts of arylsulfonylacetic acids as bleaching agents for photothermographic use. Photothermographic elements employing these thermal-dye-bleach agents are suitable for use as acutance and antihalation systems, bleachable filter dye materials, and in promoting unblocking of various components such as blocked developers.

The use of the thermally bleachable filter dye compositions of the present invention can reduce or eliminate pinholes during thermal development. Such bleachable filter dye compositions also can have the advantage of reducing or eliminating Dmin increases in the adjacent imaging layers.

Accordingly, the present invention relates to a photothermographic element comprising a support, at least one aqueous coatable photothermographic layer, and at least one aqueous coatable color filter, wherein the filer layer comprises a heat-bleachable composition comprising at least one light-absorbing filter dye that in association with a base precursor according to the present invention. Color filters are commonly used in AHU layers, magenta filter layers, and yellow filter layers, but the compositions of the present invention can be used in other layers for filtering purposes, for example, in an imaging layer.

The term "filter dye" encompasses dyes used in filter layers or antihalation layers and excludes dyes resulting from developing agents or coupling agents. In one embodiment of the invention, the particles are dispersed in a matrix comprising a hydrophilic polymer or water-dispersible hydrophobic polymer.

The invention is also directed to a method of processing a photothermographic element and the use of the photothermographic element, wherein the filter layer becomes at least 40%, preferably at least 50%, more preferably at least 90%, colorless within about 20 minutes, preferably within about 5 minutes, more preferably within about 0.5 minutes, upon heating to a temperature of at least about 90° C. (according to controlled tests of such a layer essentially alone on the same support used in the product). The described filter layer is especially advantageous because of the speed with which the layer becomes at least 40% colorless upon heating and its good shelf life storage stability. Preferred embodiments provide thermal bleaching of greater than 50% in less than 20 seconds at a temperature below 175° C.

The invention is also directed to a method of forming an image in the multicolor photothermographic element, including scanning the developed image.

DETAILED DESCRIPTION OF THE INVENTION

The base precursors of the present invention are useful in photothermographic materials which usually contain various layers and components, including imaging layers, filter layers, overcoats and the like. The base precursors comprise novel arylsulfonylacetic acid salts of guanidine bases.

One aspect of the present invention is directed to an arylsulfonylacetic acid, or photographically acceptable salt thereof, having the following structure:

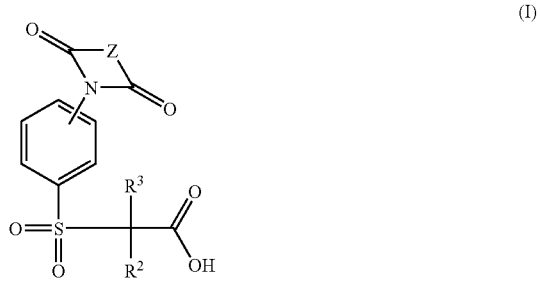

(I)

wherein the group Z individually represents the non-metallic atoms necessary to complete a substituted or unsubstituted ring system containing at least one 5- or 6-membered imide nucleus. For example, an imide ring formed by Z may include succinimide, maleimide and congeners, or fused ring systems such as phthalimide and congeners. The atoms represented by Z can also complete a 5- or 6-membered imide nucleus that can be fused with additional substituted or unsubstituted rings such as a benzo ring. For example, an imide ring formed by Z may also include 1,8-naphthalimde.

In the above Structure (I), each of $R^2$ and $R^3$ is independently a monovalent group such as hydrogen, an alkyl group, an alkenyl group, a cycloalkyl group, an aralkyl group, an aryl group and a heterocyclic group. Each of the monovalent groups may have one or more substituent groups. Among them, hydrogen, an alkyl group and an aryl group are preferred, and hydrogen is particularly preferred. Each of the alkyl group, the alkenyl group and the alkynyl group preferably has 1 to 8 carbon atoms.

Some examples of specific arylsulfonylacetic acid according to the invention are as follows:

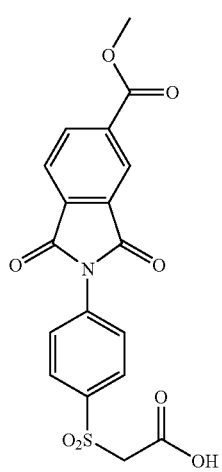

A-1

A-2
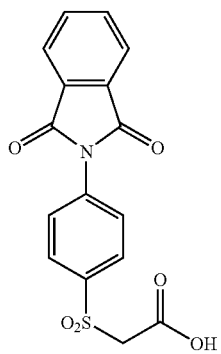
A-3
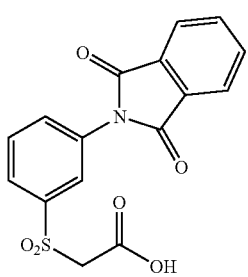
A-4
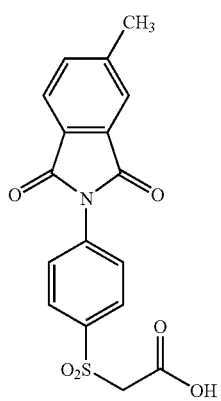
A-5
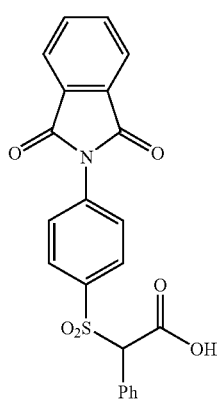
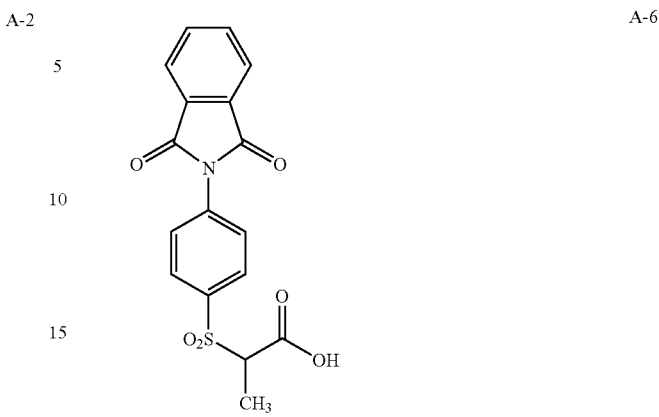
A-6
A-7
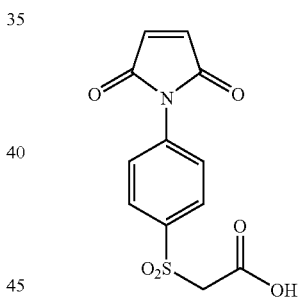
A-8
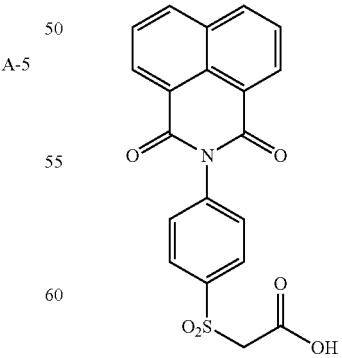
A-9
In a preferred embodiment of the present invention, the base precursors comprise the salt of an organic base with an arylsufonylacetic acid having the following structure:

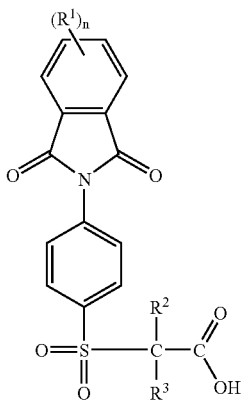

(IA)

wherein each of $R^2$ and $R^3$ is independently a monovalent group such as hydrogen, an alkyl group, an alkenyl group, a cycloalkyl group, an aralkyl group, an aryl group and a heterocyclic group. Each of the monovalent groups may have one or more substituent groups. Among them, hydrogen, an alkyl group and an aryl group are preferred, and hydrogen is particularly preferred. Each of the alkyl group, the alkenyl group and the alkynyl group preferably has 1 to 8 carbon atoms.

Each of the $R^1$ groups may be independently selected from one or more substituent groups. Examples of the substituent group include an alkyl group (preferably having 1 to 10 carbon atoms), an alkoxy group (preferably having 1 to 16 carbon atoms), a halogen atom and an alkoxycarbonyl group (preferably having 2 to 16 carbon atoms), all of which may be substituted or unsubstituted. The subscript "n" is 1 to 4, preferably 1 to 2.

These carboxylates undergo decarboxylations on heating thereby generating the arylsulfonylmethide carbanions. These carbanions in turn abstracts the acidic protons from the guanidinium moieties and strongly basic guanidines are released. The base precursor composed of a carboxylic acid and an organic base melts or is dissolved in a binder contained in a recording material at an elevated temperature and then the decarboxylation of the carboxylic acid is initiated.

The carboxylic acid of the base precursor of the present invention should have such a property that the carboxyl group undergoes decarboxylation under certain conditions. In the case that the base precursor of the present invention is used for a heat developable recording material, it is preferred that the carboxyl group undergoes decarboxylation at an elevated temperature. The heating temperature required to decarboxylate the carboxyl group preferably is in the range of 80° to 250° C., and more preferably is in the range of 110° to 200° C.

Thus, a base precursor in accordance with the present invention is in the form of a salt of an organic base with the above-described carboxylic acid. In one embodiment of the base precursor of the present invention, the organic base is a diacidic to tetraacidic base having the following Structure (II).

$$R^{13}(-B)_n \qquad (II)$$

In the Structure (II), $R^{13}$ is an n-valent residue of a hydrocarbon or heterocyclic ring, each of which may have one or more substituent groups. The "n" is an integer of 2 to 4. The "n" preferably is 2 or 4, and more preferably is 2. When the "n" is 2, it is preferred that the divalent residue of the hydrocarbon, which may constitute $R^{13}$, is an alkylene group (more preferably having 1 to 6 carbon atoms) or an arylene group (more preferably, phenylene). An example of the residue of the heterocyclic ring, which may constitute $R^{13}$, is a residue derived from pyridine ring.

The organic base preferably has a symmetrical chemical structure. Thus, it is particularly preferred that the diacidic to tetraacidic base having the Structure (III) is symmetrical. In reference to structure Structure (II), the term "symmetrical organic base" means that all of the groups represented by "B" are equivalent in the molecular structure of the organic base.

In the Structure (II), the group represented by "B" is preferably a monovalent group corresponding to an atomic group formed by removing one hydrogen atom from a "guanidine moiety" in which the organic base has two to four guanidine moieties in its molecular structure. The "guanidine moiety" corresponds to an atomic group formed by removing one or two hydrogen atoms from a compound (guanidine or a guanidine derivative) having the following Structure (III):

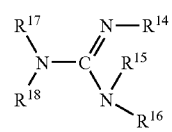

(III)

In the Structure (III), each of $R^{14}$, $R^{15}$, $R^{16}$, $R^{17}$ and $R^{18}$ are independently a monovalent group such as hydrogen, an alkyl group, an alkenyl group, an alkynyl group, a cycloalkyl group, an aralkyl group, an aryl group and a heterocyclic group. Each of the monovalent groups may have one or more substituent groups. Each of the alkyl group, alkenyl group, alkynyl group, cycloalkyl group, aralkyl group, aryl group and heterocyclic group preferably has 1 to 6 carbon atoms (including carbon atoms contained in substituent groups). Hydrogen, an alkyl group, a cycloalkyl group, an aralkyl group and an aryl group are preferred. Hydrogen and an alkyl group are more preferred. Hydrogen is most preferred. An example of the cycloalkyl group is cyclohexyl. An example of the aralkyl group is benzyl. An example of the aryl group is phenyl.

Any two of $R^{14}$, $R^{15}$, $R^{16}$, $R^{17}$ and $R^{18}$ may be combined together to form a five-membered or six-membered nitrogen containing heterocyclic ring. The heterocyclic ring preferably consists of nitrogen and carbon atoms. In other words, the five or six members of the ring preferably are only nitrogen and carbon atoms.

It is particularly preferred that the organic base or compound having the Structure (II) above is guanidine (having no substituent group), more preferably, a diacidic to tetraacidic base that is composed of two to four guanidine moieties corresponding to an atomic group formed by removing one or two hydrogen atoms from the above-mentioned compound having the Structure (III) and at least one linking group for the guanidine moieties.

The linking group is a residue of a hydrocarbon or a heterocyclic ring. The hydrocarbon may be a linear aliphatic, alicyclic or aromatic compound. Examples of the heterocyclic ring include pyridine and triazine. The linking group may have one or more substituent groups.

Examples of the substituent group include an alkyl group (preferably having 1 to 6 carbon atoms), an alkoxy group (preferably having 1 to 6 carbon atoms), a halogen atom and hydroxyl. The linking group preferably has 1 to 10 carbon atoms (including carbon atoms contained in substituent groups), more preferably has 1 to 8 carbon atoms, and most preferably has 1 to 6 carbon atoms.

The guanidine moiety preferably is a monovalent substituent group of a hydrocarbon or heterocyclic ring, as shown in the Structure (III) above. In other words, it is preferred that the guanidine moiety corresponds to an atomic group formed by removing one hydrogen atom from an guanidine having the Structure (III), but the guanidine moiety may correspond to an atomic group formed by removing two hydrogen atoms from such guanidine. In this case, the organic base may be in the form of a nitro-containing heterocyclic ring (e.g., a pyperazine ring).

Examples of the organic base which can be used in the base precursor of the present invention are given in U.S. Pat. No. 4,981,965, hereby incorporated by reference in its entirety.

In one preferred embodiment of the present invention, the salt of an organic base is a bisguanidinium salt having the following formula:

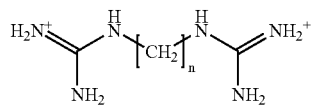

IIIA wherein n is 2, 3 or 4.

Examples of some preferred salts of organic bases are the following:

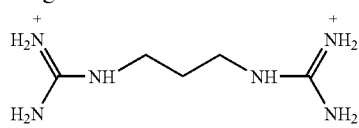

B-1

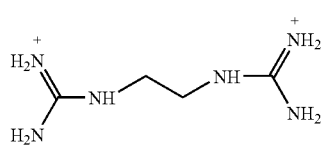

B-2

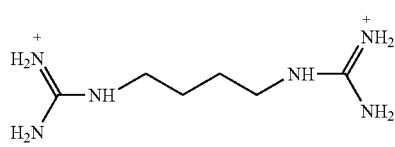

B-3

In one preferred embodiment of the invention, base precursors according to the present invention can be represented by the following Structure (IV):

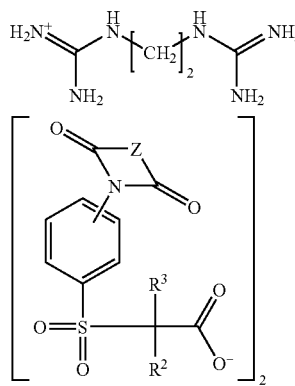

IV wherein n is 2, 3, or 4 and Z, $R^2$ and $R^3$ are as defined above with respect to Structure (I).

Some examples of some specific preferred base precursors are as follows:

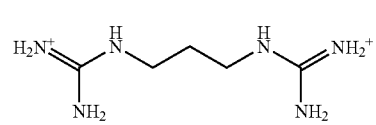

BP-1

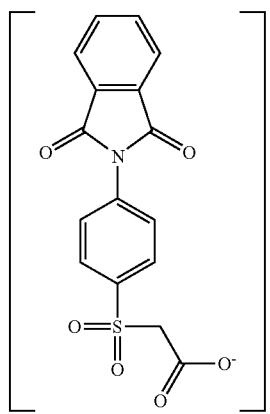

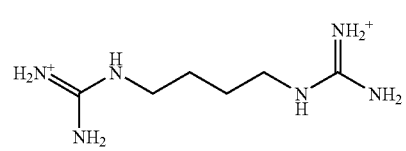

BP-2

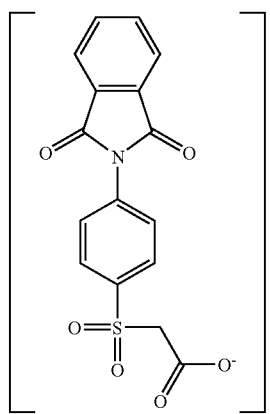

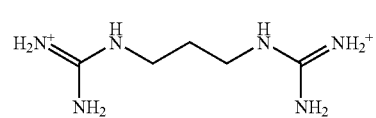

BP-3

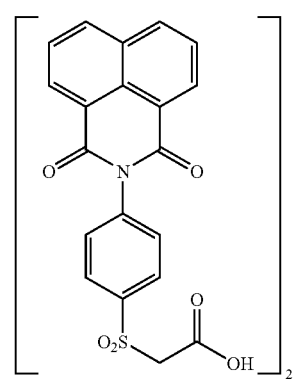

-continued

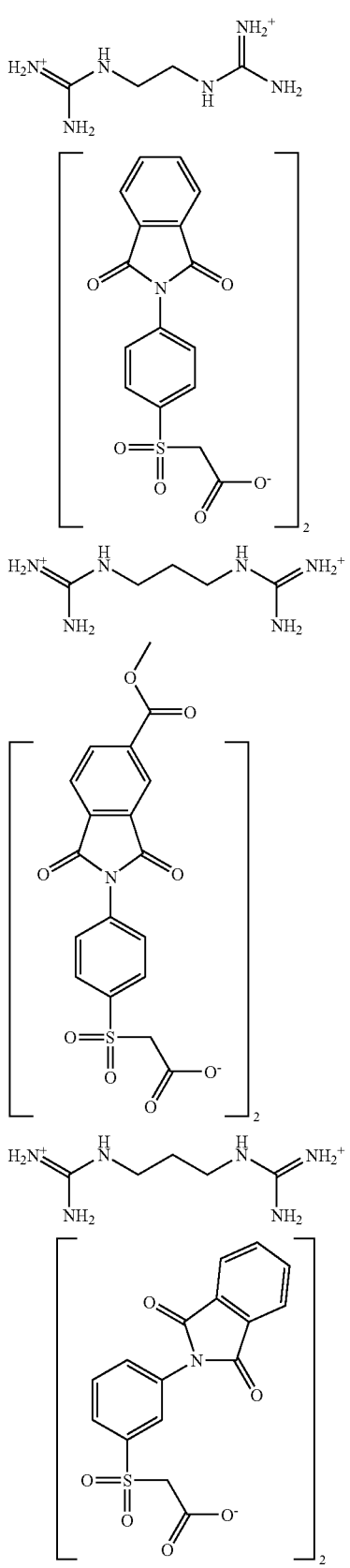

In one embodiment of the invention, base precursors in accordance with the present invention are useful for promoting reactions that require an alkaline environment, for example the unblocking of a blocked photographically useful compound. Such compounds include, but are not limited to, couplers, development inhibitors, bleach accelerators, bleach inhibitors, inhibitor releasing developers, dye precursors, developing agents, electron transfer agents, silver halide solvents, silver halide complexing agents, reductones, image toners, pre-processing or post-processing image stabilizers, hardeners, or precursors thereof.

In one embodiment of the invention, base precursors in accordance with the present invention are useful in a filter layer of a photothermographic element to absorb light of a color not completely absorbed by a color layer or color layer unit above the filter layer, while transmitting light of a color intended to be absorbed by a color layer or a color layer below the filter layer. A filter layer will typically employ a filter dye, which absorbs, or filters out, light not intended to be absorbed by a color layer. An antihalation dye can be viewed as a type of filter layer positioned below all the color layers, although no light needs to be transmitted to any color layer below the antihalation layer. In any case, however, it is necessary that passage of light through the antihalation unit (namely, back through the antihalation unit by reflection) is prevented or minimized. Thus, it may be said that filter-dye compositions absorb light from different regions of the spectrum, such as red, blue, green, ultraviolet, and infrared, to name a few, and that such filter-dye compositions perform the function of absorbing light during exposure of the material so as to prevent or at least inhibit light of a specific spectral region from reaching at least one of the radiation sensitive layers of the element. Dyes are also used in color photographic materials as filters, typically located in overcoats or interlayers, to absorb incident radiation and improve image sharpness.

It is generally desirable for both photothermographic and conventional wet-processed films to employ light-filtering filter-dye compositions that can be quickly and readily rendered ineffective, i.e., decolorized or destroyed and removed, either prior to, during, or after photographic processing.

Imaging elements that can be processed, after imagewise exposure, by heating the element are referred to as photothermographic elements. Although not essential, it would be desirable for a filter layer in a photothermographic element to be capable of being rendered substantially decolorized upon heat processing in order to avoid unwanted absorption of light during subsequent scanning. Such unwanted absorption might otherwise cause an undesirably higher level of minimum density (an increased "$D_{min}$"). Particularly in the case of a color photothermographic film, bleaching a filter layer to colorless or less colored and avoiding or minimizing any tint, subsequent to image capture but prior to scanning, is desirable.

The de-coloration or destruction of a light-absorbing dye will hereinafter be referred to as bleaching. In the case of photothermographic films, which are processed in the absence of processing baths, in the simplest case the bleaching must occur by heating.

Prior-art dyes having desirable absorption characteristics for use as a filter dye have not always had good thermal-bleaching characteristics. Visible images made from photographic elements containing such dyes have been subject to undesirable stains. Other prior-art thermally bleachable dye compositions have not had the desired stability that is required for normal storage of the photographic element, particularly when such dyes are used in combination with a base precursor subject to premature base release. Many otherwise dry photographic processes (i.e., those photographic processes that require no liquids for the preparation of a visible image) have employed light-absorbing dyes that could only be removed by subjecting them to some form of liquid treatment for example, an acid bath or an alkaline bath. However, many of these otherwise dry processes lose their attractiveness when liquids are required for dye removal. Typical processes employing prior-art light-absorbing layers are described in U.S. Pat. No. 3,260,601 and U.S. Pat. No. 3,282,699, herein incorporated by reference.

A further problem is that dark keeping of a thermally bleachable dye composition is especially challenging in the case of a photothermographic color film for consumer use. For such compositions to be useful, it would be crucial that they have the least amount of dark-keeping loss, and at the same time undergo almost complete bleaching at higher temperatures.

A variety of filter compositions have been reported in the literature for use in photothermographic systems, which compositions avoid the use of processing solutions. For example, prior patents or publications of relevance include U.S. Pat. No. 5,312,721, EP 708,086 A1, EP 911,693 A1, U.S. Pat. No. 4,981,965, U.S. Pat. No. 5,258,274, U.S. Pat. No. 4,197,131, Research Disclosure, 1978, 170, 40–41, Research Disclosure, 1978, 169, 44–45, Research Disclosure, 16978 (1978), Research Disclosure, 19721 (1980), hereby all incorporated by reference in their entirety.

The use of base precursors for use in combination with filter dyes (as antihalation layers) in photothermographic and thermographic systems are generally known. They can be used in heat processable photosensitive elements that can be constructed so that after exposure, they can be processed in a substantially dry state, or with small amounts of water, by applying heat. Because of the much greater challenges involved in developing a dry or substantially dry color photothermographic system, however, most of the activity and success to date has been limited to black-and-white photothermographic systems, especially in the areas of health imaging and microfiche.

In general, when reference in this application is made to a particular moiety or group it is to be understood that such reference encompasses that moiety whether unsubstituted or substituted with one or more substituents (up to the maximum possible number). For example, "alkyl" or "alkyl group" refers to a substituted or unsubstituted alkyl, while "benzene group" refers to a substituted or unsubstituted benzene (with up to six substituents). Generally, unless otherwise specifically stated, substituent groups usable on molecules herein include any groups, whether substituted or unsubstituted, which do not destroy properties necessary for the photographic utility. Examples of substituents on any of the mentioned groups can include known substituents, such as: halogen, for example, chloro, fluoro, bromo, iodo; hydroxy; alkoxy, particularly those "lower alkyl" (that is, with 1 to 6 carbon atoms, for example, methoxy, ethoxy; substituted or unsubstituted alkyl, particularly lower alkyl (for example, methyl, trifluoromethyl); thioalkyl (for example, methylthio or ethylthio), particularly either of those with 1 to 6 carbon atoms; substituted or unsubstituted alkenyl, preferably of 2 to 10 carbon atoms (for example, ethenyl, propenyl, or butenyl); substituted and unsubstituted aryl, particularly those having from 6 to 20 carbon atoms (for example, phenyl); and substituted or unsubstituted heteroaryl, particularly those having a 5 or 6-membered ring containing 1 to 3 heteroatoms selected from N, O, or S (for example, pyridyl, thienyl, furyl, pyrrolyl); acid or acid salt groups such as any of those described below; hydroxylate, amino, alkylamino, cyano, nitro, carboxy, carboxylate, acyl, alkoxycarbonyl, aminocarbonyl, sulfonamido, sulfamoyl, sulfo, sulfonate, alkylammonium, and an ionizable group with a pKa value below 4 in water; and others known in the art. Alkyl substituents may specifically include "lower alkyl" (that is, having 1–6 carbon atoms), for example, methyl, ethyl, and the like. Further, with regard to any alkyl group or alkylene group, it will be understood that these can be branched or unbranched and include ring structures.

The combination of a dye with an improved base precursor of the present invention, as mentioned above, finds particular utility as antihalation or acutance constructions in photothermographic materials, e.g., dry silver materials, since the dyes will readily bleach during the thermal processing of the materials. In principle, the dye may be any dye capable of being bleached by the base precursors of the invention.

Other bleachable dyes include benzothiazines [cite other docket]; cyanines as disclosed in US EP0911693, hereby incorporated by reference, polymethine dyes, and other dyes capable of being bleached by the thermal-carbanion-generating agents of the invention. One preferred class of dyes are polymethine dyes. These are disclosed, for example, in W. S. Tuemmler and B. S. Wildi, J. Amer. Chem. Soc. 1958, 80, 3772; H. Lorenz and R. Wizinger, Helv. Chem. Acta. 1945, 28, 600; U.S. Pat. Nos. 2,813,802, 2,992,938, 3,099,630, 3,275,442, 3,436,353 and 4,547,444; and Japanese Patent No. 56109,358. The dyes have found utility in infrared screening compositions, as photochromic materials, as sensitizers for photoconductors, and as infrared absorbers for optical data storage media. Polymethine dyes have been shown to bleach in conventional photographic processing solutions, as disclosed in European Patent Publication No. EP 0,377,961, but have not previously been known to bleach by thermal-carbanion-generating processes.

One preferred class of dyes are barbituric acid arylidene dyes that undergo efficient thermal bleaching in the presence of base precursors in gelatin coatings. In one preferred embodiment, arylidene dyes can be represented by the following Structure (I):

(I)

wherein A is derived from an acidic moiety, and D and R are as defined below. The acidic moiety comprises a cyclic ketomethylene moiety. Examples of a cyclic ketomethylene moiety is barbituric acid and substituted or unsubstituted derivatives thereof. In a particularly preferred embodiment, the A group is represented by the following structure (II):

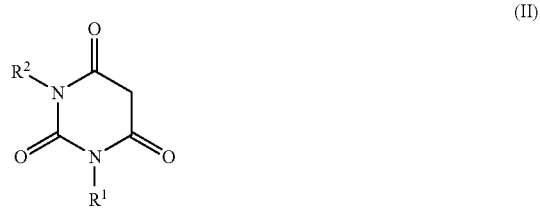

(II)

wherein $R^1$ and $R^2$ each individually represent a hydrogen, an alkyl group ("group" wherever used in the present application including the possibility of being substituted or unsubstituted alkyl) of 1 to 20 (preferably 1 to 8) carbon atoms; or an aryl, aralkyl, heterocyclic or cycloalkyl group of 5 to 14 carbon atoms.

The group R in the above structure I represents hydrogen, an aryl group containing 6 to 14 carbon atoms, or an alkyl group containing 1 to 12 carbon atoms (which groups may be substituted). The group D in the above structure I may be an aryl or heteroaryl ring. The group D may preferably contains an atom with an available electron pair positioned in conjugation (with the carbonyl oxygens of the barbituric acid ring when A represents a barbituric acid nucleus in Formula I), said atom being an O, N, Se, S in a ring system or as a substituent on such a ring. D may particularly contain an O or N atom positioned in a ring in conjugation. By being positioned in "conjugation" with the carbonyl oxygen, it is meant that there is a conjugated system between the oxygen and the atom in D. Such systems are generally known in organic chemistry and refer to a chain in which a single bond, and a double or triple bond, appear alternately.

Some examples of preferred groups for D include:

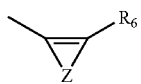
(III A)

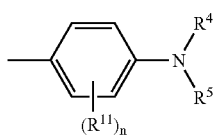
(III B)

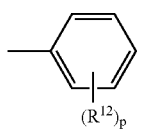
(III C)

The groups $R^6$, $R^{11}$ and $R^{12}$ each individually represents hydrogen, carboxy, carboxyalkyl, sulfonamido, sulfamoyl, or an alkyl, arylalkyl, cycloalkyl, alkoxy, alkylamino, or alkylthio group preferably of 1 to 10 carbon atoms. The groups $R^4$ and $R^5$ each individually represents an alkyl group, such as $CHR^{11}R^{12}$, preferably of 1 to 20 (and more preferably 1 to 8) carbon atoms or an alkenyl group preferably of 2 to 8 carbon atoms, or an aryl, arylalkyl, heterocyclic or cycloalkyl group preferably of 5 to about 14 carbon atoms. Alternatively, $R^4$ and $R^5$ together represent the non-metallic atoms required to form a substituted or unsubstituted 5- or 6-membered ring with each other, or $R^4$ and $R^5$ individually represent the non-metallic atoms necessary to form a substituted or unsubstituted 5- or 6-membered fused ring with the phenyl ring to which the nitrogen is attached. Preferred substituents, particularly on alkyl groups include carboxy, carboxyalkyl and sulfonamido.

The subscript "n" is 0, 1, 2, 3 or 4, preferably zero; the subscript "p" is 0, 1, 2, 3, 4 or 5, preferably 1 to 3.

The group Z individually represents the non-metallic atoms necessary to complete a substituted or unsubstituted ring system containing at least one 5- or 6-membered heterocyclic nucleus. For example, a ring system formed by Z may include pyridine, pyrazole, pyrrole, furan, thiophene, and congeners, or fused ring systems such as indole, benzoxazole, and congeners. The atoms represented by Z can also complete a 5- or 6-membered heterocyclic nucleus that can be fused with additional substituted or unsubstituted rings such as a benzo ring. Suitable heterocyclic nuclei are of the type commonly used in sensitizing dyes and are well known in the art. Many are described, for example, in James, *The Theory of the Photographic Process*, 4th Edition, pages 195–203. Useful heterocyclic nuclei include thiazole, selenazole, oxazole, imidazole, indole, benzothiazole, benzindole, naphthothiazole, naphthoxazole, benzimidazole, and the like. In a preferred embodiment, Z represents the atoms necessary to complete a substituted or unsubstituted benzoxazole or benzothiazole nucleus.

Examples of any of the alkyl groups mentioned above are methyl, ethyl, propyl, isopropyl, butyl, isobutyl, t-butyl, pentyl, hexyl, octyl, 2-ethylhexyl, and congeners. Cycloalkyl groups can be cyclopentyl, cyclohexyl, 4-methylcyclohexyl, and congeners. Alkenyl groups can be vinyl, 1-propenyl, 1-butenyl, 2-butenyl, and congeners. Aryl groups can be phenyl, naphthyl, styryl, and congeners. Arylalkyl groups can be benzyl, phenethyl, and congeners. Useful substituents on any of the foregoing or other groups disclosed, include halogen, alkoxy, acyl, alkoxycarbonyl, aminocarbonyl, carbonamido, carboxy, sulfamoyl, sulfonamido, sulfo, nitro, hydroxy, amino and congeners.

In a preferred embodiment, the compounds of Structure I above are barbituric acid arylidene dyes represented by the

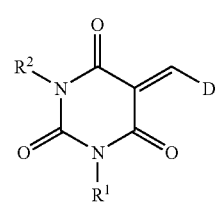
(IV)

In a preferred embodiment, D is selected from the following groups:

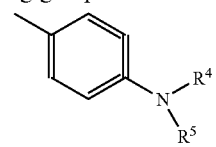
(V A)

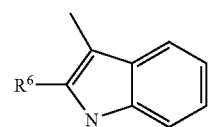
(V B)

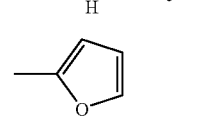
(V C)

Structures of some exemplary barbituric acid arylidene dyes are as follows:

D-1

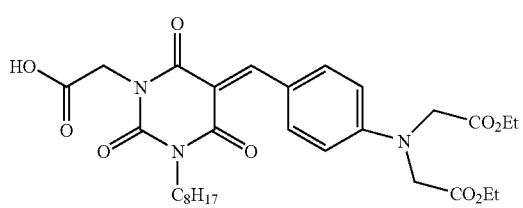

-continued
D-2 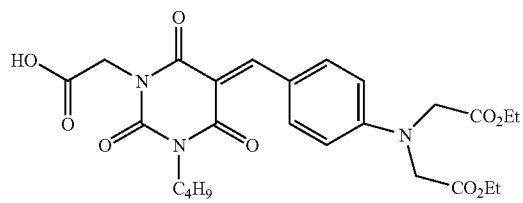
D-3 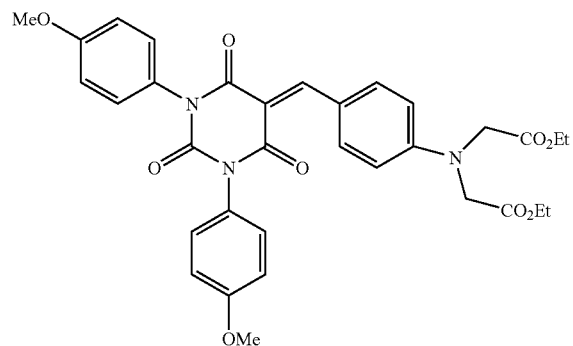
D-4 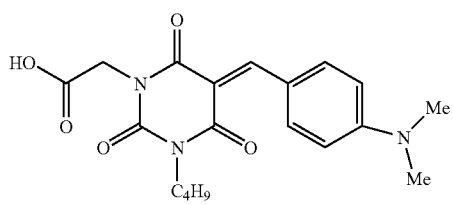
D-5 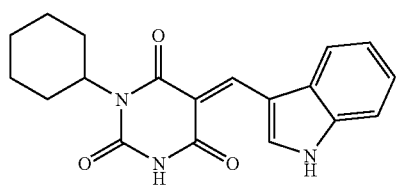
D-6 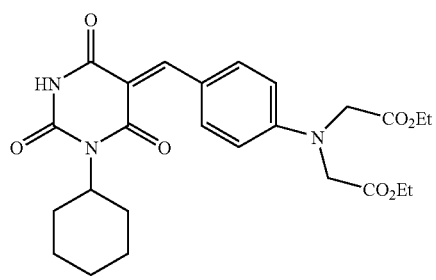
D-7 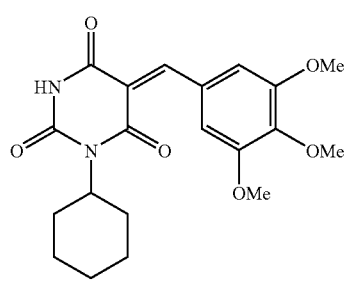

| | |
|---|---|
| D-8 | 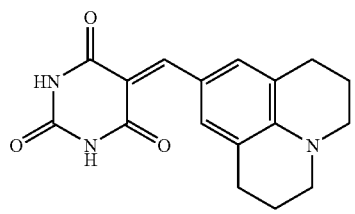 |

In a preferred embodiment, as indicated above, the above dyes are used as a yellow or magenta filter dye in a photothermographic element. The dyes such as D-1, D-2, D-3, D-4, D-5, D-6 and D-7 are suitable as yellow filter dyes. The dye D-8 may be suitable as a magenta filter dye. The barbituric acid arylidene dyes undergo efficient thermal bleaching in the presence of base precursors of the present invention.

As indicated above, in principle, any dye capable of being bleached by the base precursors of the invention can be employed.

If desired, a combination of dye compounds can be used. Selection of the dye combinations will depend upon such factors as the processing conditions, desired degree of bleaching in the layer containing the dye or dyes, solubility characteristics of the components, spectral absorption characteristics, and the like.

The filter dye should be changed to the extent that at least about 40%, and preferably at least 50%, more preferably at least 60%, still more preferably at least 80%, and most preferably at least 90% of the layer absorption is changed from colored to colorless according to a standard test using Status M density. Thus, the filter layer, after bleaching, has minimal or substantially no optical density that will adversely affect the Dmin of the product during scanning, or during overall picture production using the photothermographic element.

More than one type of filter dye can be used in the same filter layer. Combinations of different filter dyes can be used in the same layer or in different layers, depending on the purpose of the dye. Preferably, the filter dyes useful in an filter layer according to the present invention, if yellow, absorbs mainly from about 400 to about 500 nm and will transmit most of the light in the range 500 to 850 nm. Preferably, a yellow filter dye will absorb mainly at from about 420 to about 480 nm and will transmit most of the light in the range 490 to 850 nm. Similarly, a magenta filter dye will absorb light mostly from 500 to 600 nm and preferably from 520 to 580 nm while transmitting most of the light shorter than 500 nm and longer than 600 nm.

Optional means, which may be additional to bleachable filter dyes, for absorbing yellow include Carey Lea silver or a yellow processing solution decolorizable dye. Other suitable yellow filter dyes can be selected from among those illustrated by *Research Disclosure* I, Section VIII. Absorbing and scattering materials, B. Absorbing materials.

The filter dyes within the photothermographic elements can be irreversibly bleached upon exposure to heat of adequate intensity, including dry processing, in the presence of the improved base precursors of the present invention.

For black & white or monochromatic imaging elements, the phototographic elements are typically based on organic silver salt oxidizing agents and organic reducing agents are described in Owen U.S. Pat. No. 2,910,377, wherein are included silver behenate and silver stearate as well as the silver salts of a number of other organic acids, viz oleic, lauric, hydroxystearic, acetic, phthalic, terephthalic, butyric, m-nitrobenzoic, salicylic, phenylacetic, pyromellitic, p-phenylbenzoic, undecylenic, camphoric, furoic, acetamidobenzoic, and o-aminobenzoic. Other organic silver salts capable of providing similar effects include the silver salts of saccharin, benzotriazole, phthalazinone, 4'-n-octadecyloxydiphenyl-4-carboxylic acid, 10,12,14-octadecatrienoic acid, and benzoic acid. The silver salts of those organic acids which are water-insoluble and normally solid are preferred, since the byproducts do not adversely affect the coating.

Filter dye compositions in accordance with ththe present invention have good incubation stability, allowing their incorporation into elements requiring prolonged storage. The dyes contained in the novel photothermographic elements of this invention are irreversibly bleached upon exposure to heat. The amount of heat required to cause bleaching of the layers is somewhat dependent upon the particular dye incorporated in the layer; higher temperatures require shorter times to bring about bleaching while lower temperatures require longer times. Generally, temperatures of at least 125° C. for a period of at least 5 seconds are required to bring about any noticeable bleaching. For color photothermography, temperatures of 130° C. and above and times in excess of 10 seconds are generally preferred.

The dyes incorporated in the novel layers of this invention are characterized by their good spectral absorption properties. The maximum absorption of the various individual dyes ranges throughout the visible regions of the spectrum.

The dyes described herein can be used to make light-absorbing layers including filter layers with or without dyes of other classes and can be incorporated readily in colloidal binders used for forming such layers. They are especially useful in gelatin layers lying adjacent to silver halide layers.

The photographic elements prepared according to the instant invention can be used in various kinds of photothermographic systems. In addition to being useful in X-ray and other non-optically sensitized systems, they can also be used in orthochromatic, panchromatic and infrared sensitive systems. The sensitizing addenda can be added to photographic systems before or after any sensitizing dyes which are used.

The dyes used in this invention can be used in emulsions intended for color photothermography, for example, emulsions containing color-forming couplers or other color-generating materials, emulsions of the mixed-packet type such as described in U.S. Pat. No. 2,698,794 of Godowsky issued Jan. 4, 1955; in silver dye-bleach systems; and emulsions of the mixed-grain type such as described in U.S. Pat. No. 2,592,243 of Carroll and Hanson issued Apr. 8, 1952.

Photographic layers containing filter dyes can also be used in color transfer processes which utilize the diffusion transfer of an imagewise distribution of developer, coupler or dye from a light-sensitive layer to a second layer while the two layers are in close proximity to one another. Color transfer processes of this type are described in Yutzy, U.S. Pat. No. 2,856,142; Land et al. U.S. Pat. No. 2,983,606;

Whitmore et al. British Pat. Nos. 904,364 and 840,731; and Whitmore et al. U.S. Pat. No. 3,227,552.

Depending on the choice of the filter dye, it can be in the filter layer in the form of solid particles, dissolved in a dispersed organic phase, emulsified, or dissolved in the aqueous matrix of the filter layer. Although dissolving a water-soluble dye in the aqueous matrix is easiest, it is not universally preferred since one would generally prefer that the dye remain in the layer in which it was coated.

The coverages and proportions of the components which comprise the described filter component of the present invention can vary over wide ranges depending upon such factors as the particular use, location in the element of the filter component, the desired degree of absorption, processing temperatures, and the like. For example, in some photothermographic elements the concentration of dye is sufficient to provide a peak optical density of at least about 0.05. Particles of the filter dyes can be made by conventional dispersion techniques, such as milling, by preparing the particles by a limited coalescence procedure, or other procedures known in the art. Milling processes that can be used include, for example, processes described in U.K. Patent No. 1,570,632, and U.S. Pat. Nos. 3,676,147, 4,006,025, 4,474,872 and 4,948,718, the entire disclosures of which are incorporate herein by reference. Limited coalescence procedures that can be used include, for example, the procedures described in U.S. Pat. Nos. 4,994,3132, 5,055,371, 2,932,629, 2,394,530, 4,833,060, 4,834,084, 4,965,131 and 5,354,799, the entire disclosures of which are incorporated herein by reference. A suitable average size of the particles are 10 to 5000 nm, preferably 20 to 1000 nm, most preferably 30 to 500 nm.

In a preferred embodiment, the filter dye is dispersed in the binder in the form of a solid particle dispersion. Such dispersions can be formed by either milling the dye in solid form until the desired particle size range is reached, or by precipitating (from a solvent solution) the dye directly in the form of a solid particle dispersion. In the case of solid particle milling dispersal methods, a coarse aqueous premix, containing the barbituric acid arylidene compound and water, and optionally, any desired combination of water soluble surfactants and polymers, is made, and added to this premix prior to the milling operation. The resulting mixture is then loaded into a mill. The mill can be, for example, a ball mill, media mill, jet mill, attritor mill, vibratory mill, or the like. The mill is charged with the appropriate milling media such as, for example, beads of silica, silicon nitride, sand, zirconium oxide, yttria-stabilized zirconium oxide, alumina, titanium, glass, polystyrene, etc. The bead sizes typically range from 0.25 to 3.0 mm in diameter, but smaller media may be used if desired. The solid barbituric acid arylidene in the slurry are subjected to repeated collisions with the milling media, resulting in crystal fracture and consequent particle size reduction.

The aqueous dispersion can further contain appropriate surfactants and polymers previously disclosed for use in making pH precipitated dispersions. For solvent precipitation, a solution of the dye is made in some water miscible, organic solvent. The solution of the dye is added to an aqueous solution containing appropriate surfactants and polymers to cause precipitation as previously disclosed for use in making solvent precipitated dispersions.

Surfactants and other additional conventional addenda may also be used in the dispersing process described herein in accordance with prior art solid particle dispersing procedures. Such surfactants, polymers and other addenda are disclosed in U.S. Pat. Nos. 5,468,598, 5,300,394, 5,278,037, 4,006,025, 4,924,916, 4,294,917, 4,940,654, 4,950,586, 4,927,744, 5,279,931, 5,158,863, 5,135,844, 5,091,296, 5,089,380, 5,103,640, 4,990,431, 4,970,139, 5,256,527, 5,015,564, 5,008,179, 4,957,857, and 2,870,012, British Patent specifications Nos. 1,570,362 and 1,131,179 referenced above, the disclosures of which are hereby incorporated by reference, in the dispersing process of the filter dyes.

Additional surfactants or other water soluble polymers may be added after formation of the dye dispersion, before or after subsequent addition of the small particle dispersion to an aqueous coating medium for coating onto a photographic element support. The aqueous medium preferably contains other compounds such as stabilizers and dispersants, for example, additional anionic nonionic, zwitterionic, or cationic surfactants, and water soluble binders such as gelatin as is well known in the photographic element art. The aqueous coating medium may further contain other dispersion or emulsions of compounds useful in photography. Another technique for forming solid dye particles involves solvent precipitation. For example, a solution of the dye can be made in some water miscible, organic solvent, after which the solution of the dye can be added to an aqueous solution containing appropriate surfactants and polymers to cause precipitation.

Various techniques for forming a liquid dispersion of the filter dye, including oil-in-water emulsions, are well known by the skilled artisan. An oil-in-water dispersion of the dye may be prepared by dissolving the dye in an organic liquid, forming a premix with an aqueous phase containing dispersing aids such as water-soluble surfactants, polymers and film forming binders such as gelatin, and passing the premix through a mill until the desired particle size is obtained. The mill can be any high energy device such as a colloid mill, high pressure homogenizer, ultrasonic device, or the like. Preparation of conventional oil-in-water dispersions are well known in the art and are described in further detail, for example, in Jelly and Vittum U.S. Pat. No. 2,322,027. Alternatively, the filter dye can be loaded into a latex polymer, either during or after polymerization, and the latex can be dispersed in a binder. Additional disclosure of loaded latexes can be found in Milliken U.S. Pat. No. 3,418,127.

In a preferred embodiment, the base precursor is also dispersed in the binder as a solid particle dispersion. All prior descriptions of dispersion milling techniques, formulations and procedures that have described the incorporation of the filter dye are also applicable to incorporation of the base precursor.

For aqueous imaging systems, the binders used in the aqueous dispersion or coating composition should be transparent or translucent and include those materials which do not adversely affect the reaction which changes the dye from colored to colorless and which can withstand the processing temperatures employed. These polymers include, for example, proteins such as gelatin, gelatin derivatives, cellulose derivatives, polysaccharides such as dextran and the like; and synthetic polymeric substances such as water soluble polyvinyl compounds like poly(vinyl alcohol), poly (vinyl pyrrolidone), acrylamide polymers and the like. Other synthetic polymeric compounds which can be useful include dispersed vinyl compounds such as styrene butadiene rubbers in latex form. Effective polymers include high molecular weight materials, polymers and resins which are compatible with the imaging materials of the element. Combinations of the described colloids and polymers can also be useful if desired.

A preferred embodiment of the invention is a photothermographic element comprising (a) a support having thereon (b) a photothermographic layer, and on the support or in the support (c) at least one filter dye compound represented by the Structure (I), as described above, wherein the dye becomes at least about 50, preferably at least 70% colorless within about 30 seconds upon heating to a temperature of at least about 150° C., as determined by standard testing described herein. Preferably the support is suitably transparent for scanning purposes.

A visible image can be developed in a photothermographic element according to the invention within a short time after imagewise exposure merely by uniformly heating the photothermographic element to moderately elevated temperatures. For example, the photothermographic element can be heated, after imagewise exposure, to a temperature within the range which provides development of the latent image and also provides the necessary temperature to cause the filter layer to change from colored to colorless. Heating is typically carried out until a desired image is developed and until the filter layer is bleached to a desired degree. This heating time is typically a time within about 1 second to about 20 minutes, such as about 1 second to about 90 seconds.

As indicated above, the filter layer as described can be useful in a variety of photothermographic elements. For example, such photothermographic elements are used in the field of microfilming, health imaging, graphic arts, consumer products, and the like. In the field of health or medical imaging, the originating exposure may be X-ray, for example, followed by the use of phosphorescent light for exposing the film. A preferred use of the present invention, however, is in consumer color photothermographic film that is to be scanned, especially scanning turbid film as when the film is scanned without first removing the silver in the film, in which situation the bleaching of the dye will contribute to a low Dmin.

The described combination of a filter dye and base precursor can be in any suitable location in the photothermographic element which provides the desired bleaching of the dye upon heating. Typically, the inventive layer must be coated on the same side of the support as the radiation sensitive layers. In one embodiment of the invention, the dye is in association with a base precursor or base precursor to promote the desired heat bleaching in the filter component. The term "in association" as employed herein is intended to mean that the described materials are in a location with respect to each other which enables the desired processing and heat bleaching and provides a more useful developed image. The term is also employed herein to mean that the filter dye and the base precursor are in a location with respect to each other which enables the desired change of the dye from colored to colorless upon heating as described. In general, the two components should be in the same layer, meaning there is no significant barrier or distance between them even if not uniformly dispersed together. Preferably, however, the filter dye and the base precursor are uniformly inter-dispersed. Alternatively, however, a sufficient amount of base precursor may transfer from an adjacent imaging layer before and during thermal processing.

A simple exemplary photothermographic element, showing one embodiment comprising filter layers and their placement in the element, can be represented as follows:

---

UV Overcoat
Blue Sensitive Layer
Yellow Filter Layer
Green Sensitive Layer
Magenta Filter Layer
Red Sensitive Layer
AHU Layer
Support

---

As indicated above, the invention is especially useful in a dry photothermographic process (or "dry thermal process"). By a "dry thermal process" is meant herein a process involving, after imagewise exposure of the photographic element, development of the resulting latent image by the use of heat to raise the temperature of the photothermographic element or film to a temperature of at least about 80° C., preferably at least about 100° C., more preferably at about 120° C. to 180° C., in a dry process or an apparently dry process. By a "dry process" is meant without the external application of any aqueous solutions. By an "apparently dry process" is meant a process that, while involving the external application of at least some aqueous solutions, does not involve an amount more than the uniform saturation of the film with aqueous solution.

This dry thermal process typically involves heating the photothermographic element until a developed image is formed, such as within about 0.5 to about 60 seconds. By increasing or decreasing the thermal processing temperature a shorter or longer time of processing is useful. Heating means known in the photothermographic arts are useful for providing the desired processing temperature for the exposed photothermographic element. The heating means can, for example, be a simple hot plate, iron, roller, heated drum, microwave heater, heated air, vapor or the like. Thermal processing is preferably carried out under ambient conditions of pressure and humidity, for simplicity sake, although conditions outside of normal atmospheric pressure and humidity are also useful.

A dry thermal process for the development of a color photothermographic film for general use with respect to consumer cameras provides significant advantages in processing ease and convenience, since they are developed by the application of heat without wet processing solutions. Such film is especially amenable to development at kiosks or at home, with the use of essentially dry equipment. Thus, the dry photothermographic system opens up new opportunities for greater convenience, accessibility, and speed of development (from the point of image capture by the consumer to the point of prints in the consumer's hands), even essentially "immediate" development in the home for a wide cross-section of consumers.

Preferably, during thermal development an internally located blocked developing agent, in reactive association with each of three light-sensitive units, becomes unblocked to form a developing agent, whereby the unblocked developing agent is imagewise oxidized on development. It is necessary that the components of the photographic combination be "in association" with each other in order to produce the desired image. The term "in association" herein means that, in the photothermographic element, the photographic silver halide and the image-forming combination are in a location with respect to each other that enables the desired processing and forms a useful image. This may include the location of components in different layers.

A typical color photothermographic element will now be described. The support for the photothermographic element can be either reflective or transparent, which is usually preferred. When reflective, the support is white and can take the form of any conventional support currently employed in color print elements. When the support is transparent, it can be colorless or tinted and can take the form of any conventional support currently employed in color negative elements-e.g., a colorless or tinted transparent film support. Details of support construction are well understood in the art. Examples of useful supports are poly(vinylacetal) film, polystyrene film, poly(ethyleneterephthalate) film, poly(ethylene naphthalate) film, polycarbonate film, and related films and resinous materials, as well as paper, cloth, glass, metal, and other supports that withstand the anticipated processing conditions. The element can contain additional layers, such subbing layers and the like. Transparent and reflective support constructions, including subbing layers to enhance adhesion, are disclosed in Section XV of *Research Disclosure* I.

The filter dyes of the present invention can be used in the AHU layer, the yellow filter layer, or the magenta filter layer in the above photothermographic element. In such an embodiment, the photosensitive layers are coated from aqueous melts on a transparent support with a (thermally bleachable) AHU (antihalation undercoat), an overcoat containing UV protection, a (thermally-bleachable) yellow filter layer between the blue-sensitized and green-sensitized records, and the magenta filter dye layer between the green-sensitized and red-sensitized layers. The magenta filter layer is typically under the green record and provides substantially no red absorption. This magenta filter layer is a non-light-sensitive interlayer located further from the support than any red-sensitized layer, and closer to the support than any green-sensitized layer. Similarly, a yellow filter layer is typically under the blue record and provides substantially no green absorption. This yellow filter layer is a non-light-sensitive interlayer located further from the support than any green-sensitized layer, and closer to the support than any blue-sensitized layer.

Photographic elements may also usefully include a magnetic recording material as described in *Research Disclosure*, Item 34390, November 1992, or a transparent magnetic recording layer such as a layer containing magnetic particles on the underside of a transparent support as in U.S. Pat. No. 4,279,945, and U.S. Pat. No. 4,302,523.

In an example (one embodiment) of a color negative film construction, each of blue, green and red recording layer units BU, GU and RU are formed of one or more hydrophilic colloid layers and contain at least one radiation-sensitive silver halide emulsion and coupler, including at least one dye image-forming coupler. It is preferred that the green, and red recording units are subdivided into at least two recording layer sub-units to provide increased recording latitude and reduced image granularity. In the simplest contemplated construction each of the layer units or layer sub-units consists of a single hydrophilic colloid layer containing emulsion and coupler. When coupler present in a layer unit or layer sub-unit is coated in a hydrophilic colloid layer other than an emulsion containing layer, the coupler containing hydrophilic colloid layer is positioned to receive oxidized color developing agent from the emulsion during development. Usually the coupler containing layer is the next adjacent hydrophilic colloid layer to the emulsion containing layer.

BU contains at least one yellow dye image-forming coupler, GU contains at least one magenta dye image-forming coupler, and RU contains at least one cyan dye image-forming coupler. Any convenient combination of conventional dye image-forming couplers can be employed. Conventional dye image-forming couplers are illustrated by *Research Disclosure* I, cited above, X. Dye image formers and modifiers, B. Image-dye-forming couplers. The photographic elements may further contain other image-modifying compounds such as "Development Inhibitor-Releasing" compounds (DIR's). Useful additional DIR's for elements of the present invention, are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,660; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

DIR compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference.

It is common practice to coat one, two or three separate emulsion layers within a single dye image-forming layer unit. When two or more emulsion layers are coated in a single layer unit, they are typically chosen to differ in sensitivity. When a more sensitive emulsion is coated over a less sensitive emulsion, a higher speed is realized than when the two emulsions are blended. When a less sensitive emulsion is coated over a more sensitive emulsion, a higher contrast is realized than when the two emulsions are blended. It is preferred that the most sensitive emulsion be located nearest the source of exposing radiation and the slowest emulsion be located nearest the support.

One or more of the layer units of the photothermographic element is preferably subdivided into at least two, and more preferably three or more sub-unit layers. It is preferred that all light sensitive silver halide emulsions in the color recording unit have spectral sensitivity in the same region of the visible spectrum. In this embodiment, while all silver halide emulsions incorporated in the unit have spectral absorptances according to invention, it is expected that there are minor differences in spectral absorptance properties between them. In still more preferred embodiments, the sensitizations of the slower silver halide emulsions are specifically tailored to account for the light shielding effects of the faster silver halide emulsions of the layer unit that reside above them, in order to provide an imagewise uniform spectral response by the photographic recording material as exposure varies with low to high light levels. Thus higher proportions of peak light absorbing spectral sensitizing dyes may be desirable in the slower emulsions of the subdivided layer unit to account for on-peak shielding and broadening of the underlying layer spectral sensitivity.

The photothermographic element may have interlayers that are hydrophilic colloid layers having as their primary function color contamination reduction-i.e., prevention of oxidized developing agent from migrating to an adjacent recording layer unit before reacting with dye-forming coupler. The interlayers are in part effective simply by increasing the diffusion path length that oxidized developing agent must travel. To increase the effectiveness of the interlayers to intercept oxidized developing agent, it is conventional practice to incorporate a reducing agent capable of reacting with oxidized developing agent. Antistain agents (oxidized developing agent scavengers) can be selected from among those disclosed by *Research Disclosure* I, X. Dye image formers and modifiers, D. Hue modifiers/stabilization, paragraph (2).

The yellow filter dye compositions, for use in IL1, of the present invention are particularly useful when one or more silver halide emulsions in GU and RU are high bromide emulsions and, hence have significant native sensitivity to blue light.

A photothermographic element may comprise a surface overcoat SOC which is a hydrophilic colloid layer that is provided for physical protection of the color negative elements during handling and processing. Each SOC also provides a convenient location for incorporation of addenda that are most effective at or near the surface of the color negative element. In some instances the surface overcoat is divided into a surface layer and an interlayer, the latter functioning as spacer between the addenda in the surface layer and the adjacent recording layer unit. In another common variant form, addenda are distributed between the surface layer and the interlayer, with the latter containing addenda that are compatible with the adjacent recording layer unit. Most typically the SOC contains addenda, such as coating aids, plasticizers and lubricants, antistats and matting agents, such as illustrated by *Research Disclosure* I, Section IX. Coating physical property modifying addenda. The SOC overlying the emulsion layers additionally preferably contains an ultraviolet absorber, such as illustrated by *Research Disclosure* I, Section VI. UV dyes/optical brighteners/luminescent dyes, paragraph (1).

Alternative layer units sequences can be employed and are particularly attractive for some emulsion choices. Using high chloride emulsions and/or thin (<0.2 µm mean grain thickness) tabular grain emulsions all possible interchanges of the positions of BU, GU and RU can be undertaken without risk of blue light contamination of the minus blue records, since these emulsions exhibit negligible native sensitivity in the visible spectrum. For the same reason, it is unnecessary to incorporate blue light absorbers in the interlayers.

A number of modifications of color negative elements have been suggested for accommodating scanning, as illustrated by *Research Disclosure* I, Section XIV. Scan facilitating features. These systems to the extent compatible with the color negative element constructions described above are contemplated for use in the practice of this invention.

It is also contemplated that the imaging element of this invention may be used with non-conventional sensitization schemes. For example, instead of using imaging layers sensitized to the red, green, and blue regions of the spectrum, the light-sensitive material may have one white-sensitive layer to record scene luminance, and two color-sensitive layers to record scene chrominance. Following development, the resulting image can be scanned and digitally reprocessed to reconstruct the full colors of the original scene as described in U.S. Pat. No. 5,962,205. The imaging element may also comprise a pan-sensitized emulsion with accompanying color-separation exposure. In this embodiment, the developers of the invention would give rise to a colored or neutral image which, in conjunction with the separation exposure, would enable full recovery of the original scene color values. In such an element, the image may be formed by either developed silver density, a combination of one or more conventional couplers, or "black" couplers such as resorcinol couplers. The separation exposure may be made either sequentially through appropriate filters, or simultaneously through a system of spatially discreet filter elements (commonly called a "color filter array").

The imaging element of the invention may also be a black and white image-forming material comprised, for example, of a pan-sensitized silver halide emulsion and a developer of the invention. In this embodiment, the image may be formed by developed silver density following processing, or by a coupler that generates a dye which can be used to carry the neutral image tone scale.

The photothermographic elements of the present invention are preferably of type B as disclosed in *Research Disclosure* I. Type B elements contain in reactive association a photosensitive silver halide, a reducing agent or developer, optionally an activator, a coating vehicle or binder, and a salt or complex of an organic compound with silver ion. In these systems, this organic complex is reduced during development to yield silver metal. The organic silver salt will be referred to as the silver donor. References describing such imaging elements include, for example, U.S. Pat. Nos. 3,457,075; 4,459,350; 4,264,725 and 4,741,992. In the type B photothermographic material it is believed that the latent image silver from the silver halide acts as a catalyst for the described image-forming combination upon processing. In these systems, a preferred concentration of photographic silver halide is within the range of 0.01 to 100 moles of photographic silver halide per mole of silver donor in the photothermographic material.

The Type B photothermographic element comprises an oxidation-reduction image forming combination that contains an organic silver salt oxidizing agent. The organic silver salt is a silver salt which is comparatively stable to light, but aids in the formation of a silver image when heated to 80° C. or higher in the presence of an exposed photocatalyst (i.e., the photosensitive silver halide) and a reducing agent.

Suitable organic silver salts include silver salts of organic compounds. Especially in the case of black and white or monochromic photothermographic films, preferred examples thereof include compounds having a carboxyl group, for example, a silver salt of an aliphatic carboxylic acid or a silver salt of an aromatic carboxylic acid. Preferred examples of the silver salts of aliphatic carboxylic acids include silver behenate, silver stearate, silver oleate, silver laureate, silver caprate, silver myristate, silver palmitate, silver maleate, silver fumarate, silver tartarate, silver furoate, silver linoleate, silver butyrate and silver camphorate, mixtures thereof, etc. Silver salts which are substitutable with a halogen atom or a hydroxyl group can also be effectively used. Preferred examples of the silver salts of aromatic carboxylic acid and other carboxyl group-containing compounds include silver benzoate, a silver-substituted benzoate such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenylbenzoate, etc., silver gallate, silver tannate, silver phthalate, silver terephthalate, silver salicylate, silver phenylacetate, silver pyromellilate, a silver salt of 3-carboxymethyl-4-methyl-4-thiazoline-2-thione or the like as described in U.S. Pat. No. 3,785,830, and silver salt of an aliphatic carboxylic acid containing a thioether group as described in U.S. Pat. No. 3,330,663.

Preferred examples of organic silver donors for color photothermography include silver salts of benzotriazole and derivative thereof as described in Japanese patent publications 30270/69 and 18146/70, for example a silver salt of benzotriazole or methylbenzotriazole, etc., a silver salt of a halogen substituted benzotriazole, such as a silver salt of 5-chlorobenzotriazole, etc., a silver salt of 1,2,4-triazole, a silver salt of 3-amino-5-mercaptobenzyl-1,2,4-triazole, of 1H-tetrazole as described in U.S. Pat. No. 4,220,709, a silver salt of imidazole and an imidazole derivative, and the like.

The photosensitive silver halide grains and the organic silver salt are coated so that they are in catalytic proximity during development. They can be coated in contiguous layers, but are preferably mixed prior to coating. Conventional mixing techniques are illustrated by *Research Disclosure*, Item 17029, cited above, as well as U.S. Pat. No. 3,700,458 and published Japanese patent applications Nos. 32928/75, 13224/74, 17216/75 and 42729/76.

Any convenient selection from among conventional radiation-sensitive silver halide emulsions can be incorporated within the layer units and used to provide the spectral absorptances of the invention. Most commonly high bromide emulsions containing a minor amount of iodide are employed. To realize higher rates of processing, high chloride emulsions can be employed. Radiation-sensitive silver chloride, silver bromide, silver iodobromide, silver iodochloride, silver chlorobromide, silver bromochloride, silver iodochlorobromide and silver iodobromochloride grains are all contemplated. The grains can be either regular or irregular (e.g., tabular). Illustrations of conventional radiation-sensitive silver halide emulsions are provided by *Research Disclosure* I, cited above, I. Emulsion grains and their preparation. Chemical sensitization of the emulsions, which can take any conventional form, is illustrated in section IV. Chemical sensitization. The emulsion layers also typically include one or more antifoggants or stabilizers, which can take any conventional form, as illustrated by section VII. Antifoggants and stabilizers.

The silver halide grains to be used in a photothermographic element may be prepared according to methods known in the art, such as those described in *Research Disclosure* I, cited above, and James, The Theory of the Photographic Process. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation. In the course of grain precipitation one or more dopants (grain occlusions other than silver and halide) can be introduced to modify grain properties.

In a photothermographic element, the silver halide is typically provided in the form of an emulsion, including a vehicle for coating the emulsion as a layer of the element. Useful vehicles include both naturally occurring substances such as proteins, protein derivatives, cellulose derivatives (e.g., cellulose esters, ethers, and both anionically and cationically substituted cellulosics), gelatin (e.g., alkali-treated gelatin such as cattle bone or hide gelatin, or acid treated gelatin such as pigskin gelatin), deionized gelatin, gelatin derivatives (e.g., acetylated gelatin, phthalated gelatin, and the like), and others as described in *Research Disclosure*, I. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers. The vehicle can be present in the emulsion in any amount useful in photographic emulsions. The emulsion can also include any of the addenda known to be useful in photographic emulsions.

While any useful quantity of light sensitive silver, as silver halide, can be employed in the elements useful in this invention, it is preferred that the total quantity be less than 10 g/m$^2$ of silver. Silver quantities of less than 7 g/m$^2$ are preferred, and silver quantities of less than 5 g/m$^2$ are even more preferred. The lower quantities of silver improve the optics of the elements, thus enabling the production of sharper pictures using the elements.

Because in one embodiment of the invention only silver development is required, color developers (p-phenylene diamines or p-aminophenolics) are not obligatory. Other developers that are capable of forming a silver image may also be used, without regard to their ability to form a colored dye. Such developers include, in addition to p-phenylene diamine developers and substituted p-aminophenols (3,5-dichloroaminophenol and 3,5-dibromoaminophenol are particularly preferred choices) but also p-sulfonamidophenols, ascorbic acid, low valent metal compounds, particularly those containing Fe(II), Cu(I), Co(II), Mn(II), V(II), or Ti(III), hydrazine derivatives, hydroxylamine derivatives, phenidones. For incorporated developers, thermally unblocking blocked developers are preferred.

In some cases, a development activator, also known as an alkali-release agent, base-release agent or an activator precursor can be useful in the described photothermographic element of the invention. A development activator, as described herein, is intended to mean an agent or a compound which aids the developing agent at processing temperatures to develop a latent image in the imaging material. Useful development activators or activator precursors are described, for example, in Belgian Pat. No. 709,967 published Feb. 29, 1968, and Research Disclosure, Volume 155, March 1977, Item 15567, published by Industrial Opportunities Ltd., Homewell, Havant, Hampshire, PO9 1EF, UK. Examples of useful activator precursors include guanidinium compounds such as guanidinium trichloroacetate, diguanidinium glutarate, succinate, malonate and the like; quaternary ammonium malonates; amino acids, such as 6-aminocaproic acid and glycine; and 2-carboxycarboxamide activator precursors.

Examples of blocked developers that can be used in photographic elements of the present invention include, but are not limited to, the blocked developing agents described in U.S. Pat. No. 3,342,599, to Reeves; *Research Disclosure* (129 (1975) pp. 27–30) published by Kenneth Mason Publications, Ltd., Dudley Annex, 12a North Street, Emsworth, Hampshire P010 7DQ, ENGLAND; U.S. Pat. No. 4,157,915, to Hamaoka et al.; U.S. Pat. No. 4,060,418, to Waxman and Mourning; and in U.S. Pat. No. 5,019,492. Particularly useful are those blocked developers described in U.S. application Ser. No. 09/476,234, filed Dec. 30, 1999, IMAGING ELEMENT CONTAINING A BLOCKED PHOTOGRAPICALLY USEFUL COMPOUND; U.S. application Ser. No. 09/475,691, filed Dec. 30, 1999, IMAGING ELEMENT CONTAINING A BLOCKED PHOTOGRAPHICALLY USEFUL COMPOUND; U.S. application Ser. No. 09/475,703, filed Dec. 30, 1999, IMAGING ELEMENT CONTAINING A BLOCKED PHOTOGRAPHICALLY USEFUL COMPOUND; U.S. application Ser. No. 09/475,690, filed Dec. 30, 1999, IMAGING ELEMENT CONTAINING A BLOCKED PHOTOGRAPHICALLY USEFUL COMPOUND; and U.S. application Ser. No. 09/476,233, filed Dec. 30, 1999, PHOTOGRAPHIC OR PHOTOTHERMOGRAPHIC ELEMENT CONTAINING A BLOCKED PHOTOGRAPHICALLY USEFUL COMPOUND.

In one embodiment of the invention, the blocked developer is preferably incorporated in one or more of the imaging layers of the imaging element. The amount of blocked developer used is preferably 0.01 to 5 g/m$^2$, more preferably 0.1 to 2 g/m$^2$ and most preferably 0.3 to 2 g/m$^2$ in each layer to which it is added. These may be color forming or non-color forming layers of the element. The blocked developer can be contained in a separate element that is contacted to the photographic element during processing.

After image-wise exposure of the imaging element, the blocked developer can be activated during processing of the imaging element by the presence of acid or base in the processing solution, by heating the imaging element during processing of the imaging element, and/or by placing the imaging element in contact with a separate element, such as a laminate sheet, during processing. The laminate sheet optionally contains additional processing chemicals such as those disclosed in Sections XIX and XX of *Research Disclosure*, September 1996, Number 389, Item 38957 (hereafter referred to as ("*Research Disclosure I*"). All sections referred to herein are sections of *Research Disclosure I*, unless otherwise indicated. Such chemicals include, for example, sulfites, hydroxylamine, hydroxamic acids and the like, antifoggants, such as alkali metal halides, nitrogen containing heterocyclic compounds, and the like, sequestering agents such as an organic acids, and other additives such as buffering agents, sulfonated polystyrene, stain reducing agents, biocides, desilvering agents, stabilizers and the like.

It is useful to include a melt-forming compound in a photothermographic element, such as in the imaging layers and in the antihalation layer or filter layer, as described. Combinations of melt-forming compounds or melt-formers can also be useful if desired. The term "melt-forming compound" as employed herein is intended to mean a compound which upon heating to the described processing temperature provides an improved reaction medium, typically a molten medium, wherein the described reaction combination can provide a better image. The exact nature of the reaction medium at processing temperatures described is not fully understood; however, it is believed that at reaction temperatures a melt occurs which permits the reaction components to better interact. Useful melt-forming compounds are typically separate components from the reaction combination, although the reaction combination can enter into the melt formation. Typically useful melt-forming compounds are amides, imides, cyclic ureas and triazoles which are compatible with other of the components of the materials of the invention. Useful melt-forming compounds are described, for example, in Research Disclosure, Vol. 150, October 1976, Item 15049 of LaRossa and Boettcher, published by Industrial Opportunities Ltd., Homewell, Havant, Hampshire, PO9 1EF, UK. As described, the filter layers of the invention can comprise a melt-forming compound if desired. A preferred melt-former is salicylanilide and similar compounds. Examples of melt formers or thermal solvents are, for example, salicylanilide, phthalimide, N-hydroxyphthalimide, N-potassium-phthalimide, succinimide, N-hydroxy-1,8-naphthalimide, phthalazine, 1-(2H)-phthalazinone, 2-acetylphthalazinone, benzanilide, and benzenesulfonamide. Prior-art base precursors are disclosed, for example, in U.S. Pat. No. 6,013,420 to Windender. Examples of toning agents and toning agent combinations are described in, for example, Research Disclosure, June 1978, Item No. 17029 and U.S. Pat. No. 4,123,282.

A range of concentration of melt-forming compound or melt-forming compound combination is useful in the heat developable photographic materials described. The optimum concentration of melt-forming compound will depend upon such factors as the particular imaging material, desired image, processing conditions and the like.

The photothermographic elements according to the invention can contain an

Photothermographic elements as described can contain addenda that are known to aid in formation of a useful image. The photothermographic element can contain development modifiers that function as speed increasing compounds, sensitizing dyes, hardeners, anti-static agents, plasticizers and lubricants, coating aids, brighteners, absorbing and filter dyes, such as described in Research Disclosure, December 1978, Item No. 17643 and Research Disclosure, June 1978, Item No. 17029.

The layers of the photothermographic element are coated on a support by coating procedures known in the photographic art, including dip coating, air knife coating, curtain coating or extrusion coating using hoppers. If desired, two or more layers are coated simultaneously.

A photothermographic element as described preferably comprises a thermal stabilizer to help stabilize the photothermographic element prior to exposure and processing. Such a thermal stabilizer provides improved stability of the photothermographic element during storage. Preferred thermal stabilizers are 2-bromo-2-arylsulfonylacetamides, such as 2-bromo-2-p-tolysulfonylacetamide; 2-(tribromomethyl sulfonyl)benzothiazole; and 6-substituted-2,4-bis(tribromomethyl)-s-triazines, such as 6-methyl or 6-phenyl-2,4-bis (tribromomethyl)-s-triazine.

Photographic elements of the present invention are preferably imagewise exposed using any of the known techniques, including those described in Research Disclosure I, Section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like). The photothermographic elements are also exposed by means of various forms of energy, including ultraviolet and infrared regions of the electromagnetic spectrum as well as electron beam and beta radiation, gamma ray, x-ray, alpha particle, neutron radiation and other forms of corpuscular wave-like radiant energy in either non-coherent (random phase) or coherent (in phase) forms produced by lasers. Exposures are monochromatic, orthochromatic, or panchromatic depending upon the spectral sensitization of the photographic silver halide. Imagewise exposure is preferably for a time and intensity sufficient to produce a developable latent image in the photothermographic element.

Once yellow, magenta, and cyan dye image records, or other combination of three distinct colors, have been formed in the processed photographic elements of the invention, conventional techniques can be employed for retrieving the image information for each color record and manipulating the record for subsequent creation of a color balanced viewable image. For example, it is possible to scan the photographic element successively within the three distinct color regions of the spectrum or to incorporate blue, green, and red light within a single scanning beam that is divided and passed through blue, green, and red filters to form separate scanning beams for each color record. A simple technique is to scan the photographic element point-by-point along a series of laterally offset parallel scan paths. The intensity of light passing through the element at a scanning point is noted by a sensor which converts radiation received into an electrical signal. Most generally this electronic signal is further manipulated to form a useful electronic record of the image. For example, the electrical signal can be passed through an analog-to-digital converter and sent to a digital computer together with location information required for pixel (point) location within the image. In another embodiment, this electronic signal is encoded with calorimetric or tonal information to form an electronic record that is suitable to allow reconstruction of the image into viewable forms such as computer monitor displayed images, television images, printed images, and so forth.

In one embodiment, a photothermographic elements can be scanned prior to any removal of silver halide from the element. The remaining silver halide yields a turbid coating, and it is found that improved scanned image quality for such a system can be obtained by the use of scanners that employ diffuse illumination optics. Any technique known in the art for producing diffuse illumination can be used. Preferred systems include reflective systems, that employ a diffusing cavity whose interior walls are specifically designed to produce a high degree of diffuse reflection, and transmissive systems, where diffusion of a beam of specular light is accomplished by the use of an optical element placed in the beam that serves to scatter light. Such elements can be either glass or plastic that either incorporate a component that produces the desired scattering, or have been given a surface treatment to promote the desired scattering.

In view of advances in the art of scanning technologies, it has now become natural and practical for photothermographic color films such as disclosed in EP 0762 201 to be scanned, which can be accomplished without the necessity of removing the silver or silver-halide from the negative, although special arrangements for such scanning can be made to improve its quality. See, for example, Simmons U.S. Pat. No. 5,391,443. Method for the scanning of such films are also disclosed in commonly assigned U.S. Ser. No. 60/211,364 and U.S. Ser. No. 60/211,061, hereby incorporated by reference in their entirety.

For example, it is possible to scan the photographic element successively within the blue, green, and red regions of the spectrum or to incorporate blue, green, and red light within a single scanning beam that is divided and passed through blue, green, and red filters to form separate scanning beams for each color record. If other colors are imagewise present in the element, then appropriately colored light beams are employed. A simple technique is to scan the photographic element point-by-point along a series of laterally offset parallel scan paths. A sensor that converts radiation received into an electrical signal notes the intensity of light passing through the element at a scanning point. Most generally this electronic signal is further manipulated to form a useful electronic record of the image. For example, the electrical signal can be passed through an analog-to-digital converter and sent to a digital computer together with location information required for pixel (point) location within the image. The number of pixels collected in this manner can be varied as dictated by the desired image quality.

The electronic signal can form an electronic record that is suitable to allow reconstruction of the image into viewable forms such as computer monitor displayed images, television images, optically, mechanically or digitally printed images and displays and so forth all as known in the art. The formed image can be stored or transmitted to enable further manipulation or viewing, such as in U.S. Ser. No. 09/592,816 titled AN IMAGE PROCESSING AND MANIPULATION SYSTEM to Richard P. Szajewski, Alan Sowinski and John Buhr.

Illustrative systems of scan signal manipulation, including techniques for maximizing the quality of image records, are disclosed by Bayer U.S. Pat. No. 4,553,156; Urabe et al U.S. Pat. No. 4,591,923; Sasaki et al U.S. Pat. No. 4,631,578; Alkofer U.S. Pat. No. 4,654,722; Yamada et al U.S. Pat. No. 4,670,793; Klees U.S. Pat. Nos. 4,694,342 and 4,962,542; Powell U.S. Pat. No. 4,805,031; Mayne et al U.S. Pat. No. 4,829,370; Abdulwahab U.S. Pat. No. 4,839,721; Matsunawa et al U.S. Pat. Nos. 4,841,361 and 4,937,662; Mizukoshi et al U.S. Pat. No. 4,891,713; Petilli U.S. Pat. No. 4,912,569; Sullivan et al U.S. Pat. Nos. 4,920,501 and 5,070,413; Kimoto et al U.S. Pat. No. 4,929,979; Hirosawa et al U.S. Pat. No. 4,972,256; Kaplan U.S. Pat. No. 4,977,521; Sakai U.S. Pat. No. 4,979,027; Ng U.S. Pat. No. 5,003,494; Katayama et al U.S. Pat. No. 5,008,950; Kimura et al U.S. Pat. No. 5,065,255; Osamu et al U.S. Pat. No. 5,051,842; Lee et al U.S. Pat. No. 5,012,333; Bowers et al U.S. Pat. No. 5,107,346; Telle U.S. Pat. No. 5,105,266; MacDonald et al U.S. Pat. No. 5,105,469; and Kwon et al U.S. Pat. No. 5,081,692. Techniques for color balance adjustments during scanning are disclosed by Moore et al U.S. Pat. No. 5,049,984 and Davis U.S. Pat. No. 5,541,645.

The digital color records once acquired are in most instances adjusted to produce a pleasingly color balanced image for viewing and to preserve the color fidelity of the image bearing signals through various transformations or renderings for outputting, either on a video monitor or when printed as a conventional color print. Preferred techniques for transforming image bearing signals after scanning are disclosed by Giorgianni et al U.S. Pat. No. 5,267,030, the disclosures of which are herein incorporated by reference. Further illustrations of the capability of those skilled in the art to manage color digital image information are provided by Giorgianni and Madden *Digital Color Management*, Addison-Wesley, 1998.

For illustrative purposes, a non-exhaustive list of photothermographic film processes involving a common dry heat development step are as follows:

1. heat development=>scan=>stabilize (for example, with a laminate)=>scan=>obtain returnable archival film.

2. heat development=>fix bath=>water wash=>dry=>scan=>obtain returnable archival film 3. heat development=>scan=>blix bath=>dry=>scan=>recycle all or part of the silver in film 4. heat development=>bleach laminate=>fix laminate=>scan=>(recycle all or part of the silver in film)

5. heat development=>bleach=>wash=>fix=>wash=>dry=>relatively slow, high quality scan In a preferred embodiment of a photothermographic film according to the present invention, the processing time to first image (either hard or soft display for customer/consumer viewing), including (i) thermal development of a film, (ii) scanning, and (iii) the formation of the positive image from the developed film, is suitably less than 5 minutes, preferably less than 3.5 minutes, more preferably less than 2 minutes, most preferably less than about 1 minute. In one embodiment, such film might be amenable to development at kiosks, with the use of simple dry or apparently dry equipment. Thus, it is envisioned that a consumer could bring an imagewise exposed photographic film, for development and printing, to a kiosk located at any one of a number of diverse locations, optionally independent from a wet-development lab, where the film could be developed and printed without any manipulation by third-party technicians. A photothermographic color film, in which a silver-halide-containing color photographic element after imagewise exposure can be developed merely by the external application of heat and/or relatively small amounts of alkaline or acidic water, but which same film is also amenable to development in an automated kiosk, preferably not requiring third-party manipulation, would have significant advantages. Assuming the availability and accessibility of such kiosks, such photothermographic films could potentially be developed at any time of day, "on demand," in a matter minutes, without requiring the participation of third-party processors, multiple-tank equipment and the like. Optional, such photographic processing could potentially be done on an "as needed" basis, even one roll at a time, without necessitating the high-volume processing that would justify, in a commercial setting, equipment capable of high-throughput. Color development and subsequent scanning of such a film could readily occur on an individual consumer basis, with the option of generating a display element corresponding to the developed color image. By kiosk is meant an automated free-standing machine, self-contained and (in exchange for certain payments) capable of developing a roll of imagewise exposed film on a roll-by-roll basis, without the intervention of technicians or other third-party persons such as necessary in wet-chemical laboratories. Typically, the customer will initiate and control the carrying out of film processing and optional printing by means of a computer interface. Such kiosks typically will be less than 6 cubic meters in dimension, preferably 3 cubic meters or less in dimension, and hence commercially transportable to diverse locations. Such kiosks may optionally comprise a heater for color development, a scanner for digitally recording the color image, and a device for transferring the color image to a display element.

The following examples are presented to illustrate the practice of this invention, but are not meant to limit it in any way. All percentages are by weight unless otherwise indicated.

EXAMPLES

The arylsulfonylacetic acid portion of BP-1 base precursor was prepared by reacting the corresponding amine (preparation described in U.S. Pat. No. 6,242,155 B1) with phthalic anhydride in glacial acetic acid in the presence of triethylamine.

4-Phthalimido-phenylsulfonylacetic acid:

The compound 4-amino-phenylsulfonylacetic acid hemisulfate salt (preparation described in U.S. Pat. No. 6,242,155 B1) (104.4 g, 0.33 mol) and phthalic anhydride (49.3 g, 0.33 mol) were combined in a 2 liter 3-neck round bottom flask, fitted with a mechanical stirrer, a thermometer and a condenser. Glacial acetic acid (1 L) was added to the mixture. Triethylamine (7.4 g, 10.1 mol) was slowly added to this suspension while being stirred at room temperature. The resulting mixture was heated to 110° C. for 3 hours, resulting in a clear solution. It was then cooled to 50° C. and ice and water were added to it—resulting in the precipitation of white solid. Kept in the refrigerator overnight. Solid was filtered, washed with water and with ligroin. It was then dried in the oven to give 56.8 g (yield 50%) of the desired 4-phthalimido-phenylsulfonylacetic acid, 97% pure by HPLC.

The base precursors of the present invention were prepared using the general procedures described in EP708086 A1 and U.S. Pat. No. 4,981,965.

Photographic Example

The following components are used in the example.

Silver Salt Dispersion SS-1:

A stirred reaction vessel was charged with 431 g of lime processed gelatin and 6569 g of distilled water. A solution containing 214 g of benzotriazole, 2150 g of distilled water, and 790 g of 2.5 molar sodium hydroxide was prepared (Solution B). The mixture in the reaction vessel was adjusted to a pAg of 7.25 and a pH of 8.00 by additions of Solution B, nitric acid, and sodium hydroxide as needed.

A 4 l solution of 0.54 molar silver nitrate was added to the kettle at 250 cc/minute, and the pAg was maintained at 7.25 by a simultaneous addition of solution B. This process was continued until the silver nitrate solution was exhausted, at which point the mixture was concentrated by ultrafiltration. The resulting silver salt dispersion contained fine particles of silver benzotriazole (AgBZT).

Silver Salt Dispersion SS-2:

A stirred reaction vessel was charged with 431 g of lime processed gelatin and 6569 g of distilled water. A solution containing 320 g of 1-phenyl-5-mercaptotetrazole, 2044 g of distilled water, and 790 g of 2.5 molar sodium hydroxide was prepared (Solution B). The mixture in the reaction vessel was adjusted to a pAg of 7.25 and a pH of 8.00 by additions of Solution B, nitric acid, and sodium hydroxide as needed.

A 4 l solution of 0.54 molar silver nitrate was added to the kettle at 250 cc/minute, and the pAg was maintained at 7.25 by a simultaneous addition of solution B. This process was continued until the silver nitrate solution was exhausted, at which point the mixture was concentrated by ultrafiltration. The resulting silver salt dispersion contained fine particles of the silver salt of 1-phenyl-5-mercaptotetrazole (AgPMT).

Silver Halide Emulsions:

The emulsions employed in these examples are silver iodobromide tabular grains precipitated by conventional means as known in the art. The magenta and cyan imaging layers use the same silver halide precipitation which yields a 1.31 µm ECD by 0.121 µm thick emulsion containing 3.7% iodide. Both emulsions have been given chemical sensitizations as known in the art to produce optimum sensitivity. The emulsion in the magenta layer is dyed with a mixture of dyes SM-1 and SM-2 in order to impart green light sensitivity (Emulsion EM-1), while the emulsion used in the cyan record is dyed with a mixture of dyes SC-1 and SC-2 in order to impart red light sensitivity (Emulsion EC-1).

Coupler Dispersion CDM-1:

An oil based coupler dispersion was prepared by conventional means containing coupler M-1, tricresyl phosphate, and 2-butoxy-N,N-dibutyl-5-(1,1,3,3-tetramethylbutyl)-Benzenamine, at a weight ratio of 1:0.8:0.2.

Coupler Dispersion CDC-1:

A coupler dispersion was prepared by conventional means containing coupler C-1 and dibutyl sebacate in a ratio of 1:1 solvents.

Antifoggant Dispersion AD-1:

A dispersion of the antifoggant AF-1 was prepared by conventional means containing antifoggant AF-1 and the solvent N,N-dibutyldodecanamide in the ratio of 1:2.

Melt Former MF-1 Dispersion (Salicylanilide):

A dispersion of salicylanilide was prepared by the method of ball milling. To a total 20 g sample was added 3.0 gm salicylanilide solid, 0.20 g polyvinyl pyrrolidone, 0.20 g Triton X 200 surfactant, 1.0 g gelatin, 15.6 g distilled water, and 20 mL of zirconia beads. The slurry was ball milled for 48 hours. Following milling, the zirconia beads were removed by filtration. The slurry was refrigerated prior to use.

For preparations on a larger scale, the salicylanilide was media-milled to give a final dispersion containing 30% Salicylanilide, with 4% Triton X 200 surfactant and 4% polyvinyl pyrrolidone added relative to the weight of Salicylanilide. In some cases the dispersion was diluted with water to 25% Salicylanilide or gelatin (5% of total) was added and the concentration of Salicylanilide adjusted to 25%. Biocide may also be added.

Blocked Developer BD-1 Dispersion:

The check dispersion was prepared by combining 3 g of BD-1 with 3 g of a 10% Olin 10G aqueous solution, 9 g of high purity water and 15 ml of 0.7 mm zirconium silicate beads. The mixture was milled for 90 minutes in a high-energy media mill. After milling, the dispersion was separated from the beads and diluted to 15% developer with high purity water. The dispersion was examined by optical microscopy immediately after milling, and after being held for 24 hours at 45° C.

Base Precursor Dispersions:

The base precursor dispersions were prepared by the method of ball milling.

The comparative base Precursor BP-C dispersion was prepared following the procedure below:

The following ingredients were combined in a 4-oz glass jar: 1.2 g of BP-C, 0.6 g of a 10% solution of the surfactant OLIN 10G in water, 1.2 g of a 10% solution of polyvinylpyrrolidone in water, 21.0 g of high purity water, and 60 mL 1.8 mm zirconium oxide ceramic beads. The jar was sealed and rolled at 65 ft/min for 3 days. Following milling, the zirconium oxide beads were removed by filtration without dilution.

The dispersion of the base precursor BP-1, in accordance with the present invention, was prepared following the procedure below:

The following ingredients were combined in a 4-oz glass jar: 0.84 g of BP-1, 1.26 g of a 10% solution of the polymeric surfactant Dapryl, 21.9 g of high purity water, and 60 mL 1.8 mm zirconium oxide ceramic beads. The jar was sealed and rolled at 65 ft/min for 3 days. Following milling, the zirconium oxide beads were removed by filtration without dilution.

The base precursors exhibited the following properties.

| ID | Solubility in water @40° C. g/100 mL | Onset Temperature of $CO_2$ loss by TGA Analysis ° C. |
|---|---|---|
| BP-C Comparative | 0.22 | 127 |
| BP-1 invention | 0.06 | 144 |

UV-1

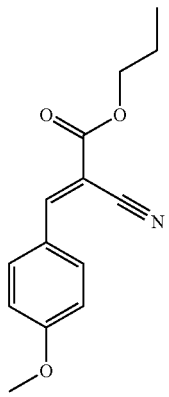

M-1

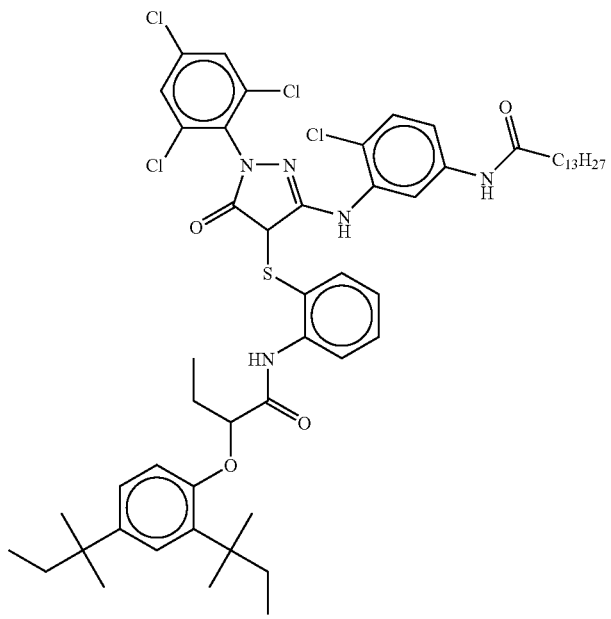

-continued
| ID | Solubility in water @40° C. g/100 mL | Onset Temperature of $CO_2$ loss by TGA Analysis ° C. |
|---|---|---|
AF-1
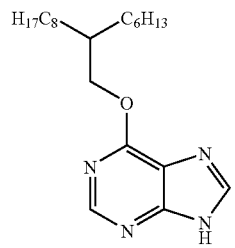
C-1
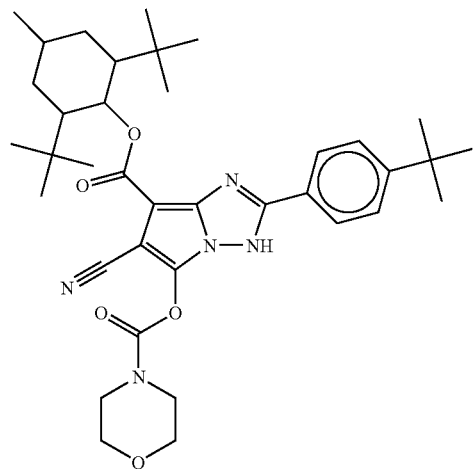
BD-C
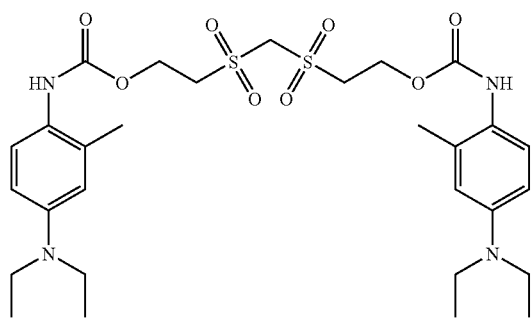
BP-C
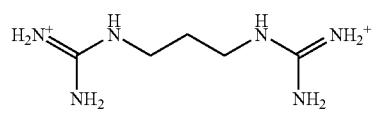
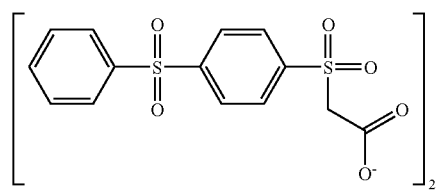

-continued
| ID | Solubility in water @40° C. g/100 mL | Onset Temperature of CO$_2$ loss by TGA Analysis ° C. |
|---|---|---|
BP-1
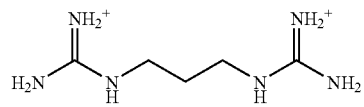
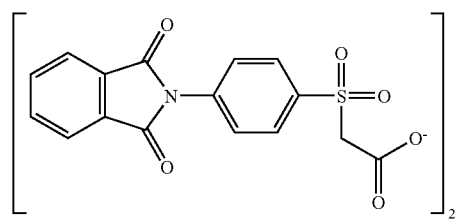
SM-1
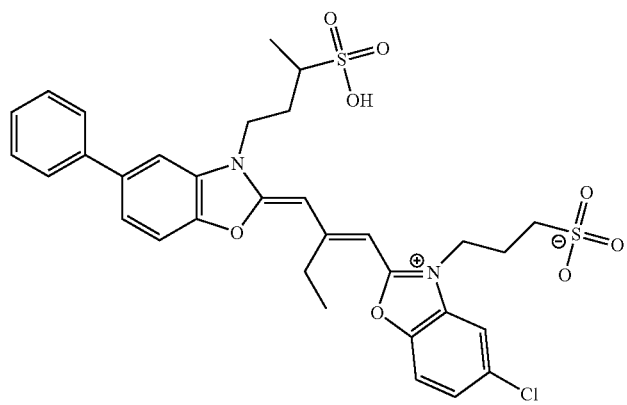
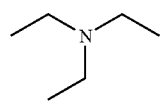
SM-2
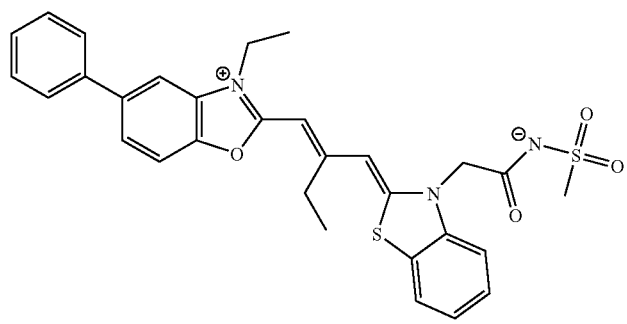

-continued
| ID | Solubility in water @40° C. g/100 mL | Onset Temperature of CO$_2$ loss by TGA Analysis ° C. |
|---|---|---|
SC-1
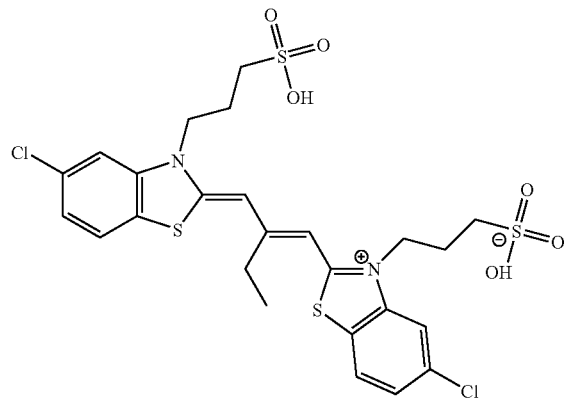
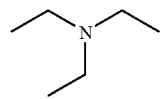
SC-2
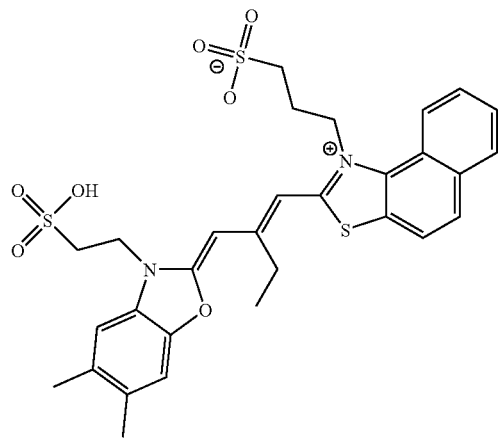
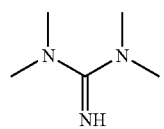
H-1
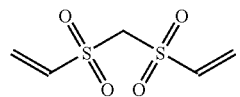

| ID | Solubility in water @40° C. g/100 mL | Onset Temperature of CO$_2$ loss by TGA Analysis ° C. |
|---|---|---|
| BYD-1 | | |

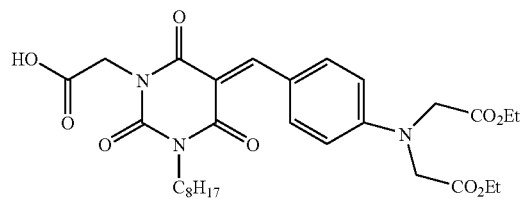

The above chemical components were incorporated into the following coating structure. All coatings were prepared on a 4.7 mil thick poly(ethylene terephthalate) support. Variations to the coating were made by adding base precursors to the Filter dye layer.

| Layer | Component | Laydown, g/m$^2$ |
|---|---|---|
| Overcoat | Gelatin | 1.076 |
| | Hardener H-1 | 0.247 |
| | Silicone Lubricant | 0.039 |
| | Polymeric Matte Beads | 0.113 |
| | UV Absorber Dye UV-1 | 0.097 |
| Magenta Imaging Layer | Gelatin | 4.304 |
| | AG-BZT (from SS-1) | 0.323 |
| | AG-PMT (from SS-2) | 0.323 |
| | Coupler M-1 (from CDM-1) | 0.538 |
| | Antifoggant AF-1 | 0.022 |
| | Melt Former MF-1 | 0.861 |
| | Blocked Developer BD-1 | 0.861 |
| | Emulsion EM-1 | 0.861 |
| Filter Dye Layer | Gelatin | 1.076 |
| | Bleachable Yellow Dye BYD-1 | 0.215 |
| Cyan Imaging Layer | Gelatin | 4.304 |
| | AG-BZT (from SS-1) | 0.323 |
| | AG-PMT (from SS-2) | 0.323 |
| | Coupler C-1 (from CDC-1) | 0.538 |
| | Antifoggant AF-1 | 0.022 |
| | Melt Former MF-1 | 0.861 |
| | Blocked Developer BD-1 | 0.861 |
| | Emulsion EC-1 | 0.861 |
| Undercoat | Gelatin | 1.614 |

The resulting coatings were exposed through a step wedge to a 3.04 log lux light source at 3000K filtered by Daylight 5A and Wratten 2B filters. The exposure time was 0.01 second. After exposure, the coating was thermally processed by contact with a heated drum for 18 seconds. The drum was maintained at a temperature of 157.5° C. After processing, the coatings were evaluated for Dmin and for the presence of pinholes. The pinholes represent areas where escaping carbon dioxide gas damages the coating and leaves microscopic areas of density lower than the surrounding areas.

The Following coatings were created in which the base precursor was placed in the filter dye layer at a level of 1.30 g/m2.

| Coating | Base Precursor | Cyan Dmin | Magenta Dmin | Pinholes |
|---|---|---|---|---|
| C-1 | None | 0.196 | 0.266 | No |
| C-2 | BP-C | 1.16 | 0.931 | Yes |
| C-3 | BP-1 | 0.196 | 0.248 | No |

As shown by the above table, the comparative base precursor BP-C led not only to significant Dmin growth in both magenta and cyan records, but also to the presence of pinholes. Image analysis showed severe pinhole formation resulting in approximately 3800 pinholes per square centimeter in the processed coating. The inventive base precursor BP-1, on the other hand, showed no Dmin signal within experimental error, as well as no pinhole formation.

The invention has been described in detail with particular reference to certain preferred embodiments thereof, but it will be understood that variations and modifications can be effected within the spirit and scope of the invention.

What is claimed is:

1. A photothermographic element comprising a support having thereon at least one coatable light-sensitive imaging layer and at least one layer comprising a base precursor comprising an organic base, and with an arylsulfonylacetic acid having the following structure:

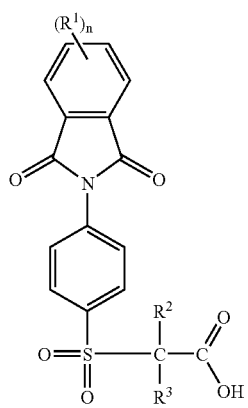

wherein each of R$^2$ and R$^3$ is a monovalent group selected from the group consisting of hydrogen, an alkyl group, an alkenyl group, a cycloalkyl group, an aralkyl group, an aryl group and a heterocyclic group, wherein each of the monovalent groups may have one or more substituent groups;

the subscript n is 1 to 4 and each of the $R^1$ groups may be independently selected from one or more substituent groups and wherein said organic base comprises two to four guanidine moieties.

2. The photothermographic element of claim 1 wherein said base precursor is in bleaching association with a filter dye.

3. The photothermographic element of claim 2 wherein said filter dye and said base precursor are both in a coatable light-absorbing layer.

4. The photothermographic element of claim 1 wherein said base precursor is in association with one or more blocked photographically useful compounds, and the base precursor is capable of promoting the unblocking of said one or more blocked photographically useful compounds.

5. The photothermographic element of claim 2 wherein the dye is a barbituric acid arylidene filter dye.

6. The photothermographic element of claim 5 wherein the arylidene filter dye is represented by the following formula:

$$A=\overset{R}{\underset{|}{C}}-D$$

wherein A comprises an acidic nucleus, comprising a cyclic ketomethylene moiety; D contains an aryl or heterocyclic moiety which may be substituted or fused, and R represents hydrogen, an aryl group containing 6 to 14 carbon atoms, or an alkyl group containing 1 to 12 carbon atoms which groups may optionally be substituted.

7. The photothermographic element of claim 6 wherein the A group is represented by the following structure:

[structure of barbituric acid with $R^1$ and $R^2$ on nitrogens]

wherein $R^1$ and $R^2$ each individually represent a hydrogen, an alkyl, aryl, aralkyl, heterocyclic or cycloalkyl group, which groups that can be substituted or unsubstituted.

8. The photothermographic element of claim 2 wherein the base precursor is capable of reacting with the dye at a temperature higher than 80° C.

9. The photothermographic element of claim 1 wherein the organic base is a diacidic to tetraacidic base having the following Structure:

$$R^{13}(-B)_n$$

wherein $R^{13}$ is an n-valent residue of a hydrocarbon or heterocyclic ring, each of which may have one or more substituent groups; "n" is an integer of 2 to 4;

and wherein "B" is a monovalent group corresponding to an atomic group formed by removing one hydrogen atom from a guanidine having the Structure:

[guanidine structure with $R^{14}, R^{15}, R^{16}, R^{17}, R^{18}$]

wherein each of $R^{14}$, $R^{15}$, $R^{16}$, $R^{17}$ and $R^{18}$ are independently a monovalent group selected from the group consisting of hydrogen, an alkyl group, an alkenyl group, an alkynyl group, a cycloalkyl group, an aralkyl group, an aryl group and a heterocyclic group, wherein each of the monovalent groups may have one or more substituent groups; or any two of $R^{14}$, $R^{15}$, $R^{16}$, $R^{17}$ and $R^{18}$ may be combined together to form a five-membered or six-membered nitrogen containing heterocyclic ring.

10. The photothermographic element of claim 9 wherein each of $R^{14}$, $R^{15}$, $R^{16}$, $R^{17}$ and $R^{18}$ is hydrogen or an alkyl group.

11. The photothermographic element of claim 9 wherein n is 2.

12. The photothermographic element of claim 9 wherein $R^{13}$ is an alkylene group or an arylene group, which may have one or more substituent groups.

13. The photothermographic element of claim 1 wherein the base precursor is a bisguanidine base precursor.

14. The photothermographic element of claim 1 wherein the base precursor is a bisguanidinium salt of an arylsulfonylacetic acid having the following formula:

[structure of bisguanidinium salt]

wherein the subscript n is 1 to 4, wherein p is 2, 3 or 4; the groups $R^2$ and $R^3$ are independently a hydrogen or a substituted or unsubstituted alkyl or aryl group; and the group $R^1$ is independently selected from hydrogen, an aryl, alkoxy, or an alkoxycarbonyl group.

15. The photothermographic element of claim 1 comprising, on the support, at least one light-sensitive silver halide emulsion layer and at least one light-absorbing non-light sensitive layer comprising a filter dye.

16. The photothermographic element of claim 2 wherein said filter dye is capable of becoming at least about 50% colorless within about 5 minutes upon heating to a temperature of at least about 90° C.

17. A photothermographic element according to claim 1 wherein the photothermographic element contains an imaging layer comprising a blocked developer, a light-sensitive silver halide emulsion, and a non-light sensitive silver salt oxidizing agent.

18. A photothermographic element according to claim 1 comprising a mixture of at least two organic silver salts, at least one of which is a non-light sensitive silver salt oxidizing agent.

19. The photothermographic element of claim 1 comprising, on the support, at least three aqueous-coatable light-sensitive imaging layers which have their individual sensitivities in different wavelength regions and also an aqueous-coatable filter layer, below the imaging layers, comprising at least one antihalation dye in association with an effective amount, for bleaching of the antihalation dye, of the base precursor, wherein said filter dye becomes at least about 50% colorless within about 5 minutes upon heating to a temperature of at least about 90° C.

20. A photothermographic process for preparing visible photographic images comprising the steps of:
 (a) providing a photothermographic element as in claim 1 comprising, coating on the support, (i) at least one aqueous-coatable layer containing photosensitive silver halide, a water-insoluble organic silver salt as an oxidizing agent, a reducing agent for silver ion, and (ii) a aqueous-coatable light-absorbing layer comprising a filter dye in association with an effective amount, for bleaching of the filter dye, of the base precursor; and
 (b) thermally developing the film step without any externally applied developing agent, comprising heating said film to an average temperature of at least 90° C. for at least 0.5 seconds, wherein said filter dye becomes at least about 50% colorless.

\* \* \* \* \*